US012788741B2

(12) United States Patent
Bazan et al.

(10) Patent No.: US 12,788,741 B2
(45) Date of Patent: Nov. 10, 2026

(54) METHODS OF TREATMENT

(71) Applicant: Board of Supervisors of Louisiana State University and Agricultural and Mechanical College, Baton Rouge, LA (US)

(72) Inventors: Nicolas G. Bazan, New Orleans, LA (US); Minghao Jin, Metairie, LA (US); Songhua Li, Metairie, LA (US)

( * ) Notice: Subject to any disclaimer, the term of this patent is extended or adjusted under 35 U.S.C. 154(b) by 515 days.

(21) Appl. No.: 18/033,283

(22) PCT Filed: Oct. 22, 2021

(86) PCT No.: PCT/US2021/056284
§ 371 (c)(1),
(2) Date: Apr. 21, 2023

(87) PCT Pub. No.: WO2022/087437
PCT Pub. Date: Apr. 28, 2022

(65) Prior Publication Data
US 2023/0390240 A1 Dec. 7, 2023

Related U.S. Application Data

(60) Provisional application No. 63/138,177, filed on Jan. 15, 2021, provisional application No. 63/104,383, filed on Oct. 22, 2020.

(51) Int. Cl.
*A61K 31/397* (2006.01)
*A61K 31/192* (2006.01)
*A61K 48/00* (2006.01)
*A61P 27/02* (2006.01)

(52) U.S. Cl.
CPC .......... *A61K 31/397* (2013.01); *A61K 31/192* (2013.01); *A61K 48/005* (2013.01); *A61P 27/02* (2018.01)

(58) Field of Classification Search
CPC .. A61K 31/397; A61K 31/192; A61K 48/005; A61P 27/02
USPC ..................................................... 514/210.17
See application file for complete search history.

(56) References Cited

U.S. PATENT DOCUMENTS

2005/0209167 A1 9/2005 Schaffner et al.

OTHER PUBLICATIONS

Clinical and Research Information on Drug-Induced Liver Injury [Internet]. Bethesda (MD): National Institute of Diabetes and Digestive and Kidney Diseases; 2012-. Antilipemic Agents. [Updated Jun. 4, 2019]. BookshelfURL: https://www.ncbi.nlm.nih.gov/books/ (Year: 2012).*
Naples et al Am. J. Physiol Gastrointest Liver Physiol, 2012, 302, G1043-G1052 (Year: 2012).*
Cicero et al Journal of Clinical Lipidology, 2020, 14, 646-648 (Year: 2020).*
NICE www.nice.org.uk/guidance/hst11 (Year: 2019).*
Jin et al Adv. Exp. Med. Biol. 2016, 854, 525-532 (Year: 2016).*
International Search Report for PCT/US2021/056284 mailed on Feb. 2, 2022.
Li et al., Fatty Acid Transport Protein 4 (FATP4) Prevents Light-Induced Degeneration of Cone and Rod Photoreceptors by Inhibiting RPE65 Isomerase. The Journal of Neuroscience, Feb. 13, 2013, 33(7):3178-3189.
Li et al., Pharmacological Amelioration of Cone Survival and Vision in a Mouse Model for Leber Congenital Amaurosis, The Journal of Neuroscience, May 25, 2016, 36(21): 5808-5819.
Naples et al., Ezetimibe ameliorates intestinal chylomicron overproduction and improves glucose tolerance in a diet-induced hamster model of insulin resistance. Am J Physiol Gastrointest Liver Physiol. May 1, 2012; 302(9).
Written Opinion of the International Search Report for PCT/US2021/056284 mailed on Feb. 2, 2022.
Acland, G. M. et al. Long-term restoration of rod and cone vision by single dose rAAVmediated gene transfer to the retina in a canine model of childhood blindness. Mol Ther 12(6), 1072-1082 (2005).
Ansel et al. Pharmaceutical dosage forms and drug delivery systems, 6th Edition, Media, PA: Williams and Wilkins (1999).
Bainbridge, J. W. et al. Effect of gene therapy on visual function in Leber's congenital amaurosis. N. Engl. J. Med. 358, 2231-2239 (2008).
Bainbridge, J. W. et al. Long-term effect of gene therapy on Leber's congenital amaurosis. N. Engl. J. Med. 372, 1887-1897 (2015).
Batten, M. L. et al. Lecithin-retinol acyltransferase is essential for accumulation of alltrans-retinyl esters in the eye and in the liver. J. Biol. Chem. 279, 10422-10432 (2004).
Bernstein, P. S. et al. Lutein, zeaxanthin, and meso-zeaxanthin: The basic and clinical science underlying carotenoid-based nutritional interventions against ocular disease. Prog. Retin. Eye Res. 50, 34-66 (2016).
Buchwald, H. et al. Long-term, continuous intravenous heparin administration by an implantable infusion pump in ambulatory patients with recurrent venous thrombosis. Surgery 88(4):507-516, (1980).
Chen, P. et al. A photic visual cycle of rhodopsin regeneration is dependent on Rgr. Nat. Genet. 28, 256-260 (2001).
Cideciyan, A. V. et al. Human gene therapy for RPE65 isomerase deficiency activates the retinoid cycle of vision but with slow rod kinetics. Proc. Natl. Acad. Sci. U. S. A. 105(39), 15112-15117 (2008).
Cideciyan, A. V. et al. Human retinal gene therapy for Leber congenital amaurosis shows advancing retinal degeneration despite enduring visual improvement. Proc. Natl. Acad. Sci. U. S. A. 110, E517-525 (2013).
Fan, J. et al. Isorhodopsin rather than rhodopsin mediates rod function in RPE65 knock-out mice. Proc. Natl. Acad. Sci. U. S. A. 100(23), 13662-13667 (2003).
(Continued)

*Primary Examiner* — Yevgeny Valenrod
(74) *Attorney, Agent, or Firm* — Baker, Donelson, Bearman, Caldwell & Berkowitz, PC

(57) ABSTRACT

Aspects of this invention is directed to compositions and methods for treating the visual cycle as well as the survival and function of cones and rods in patients with retinal degeneration.

15 Claims, 12 Drawing Sheets

(56) References Cited

OTHER PUBLICATIONS

Gennaro, A.R. (ed). Remington-The science and practice of pharmacy. 20th ed., Lippincott Williams & Wilkins, Baltimore, MD, 2000.
Golczak, M. et al. Positively charged retinoids are potent and selective inhibitors of the trans-cis isomerization in the retinoid (visual) cycle. Proc. Natl. Acad. Sci. U. S. A. 102(23), 8162-8167 (2005).
Hall, A. M. et al. Enzymatic properties of purified murine fatty acid transport protein 4 and analysis of acyl-CoA synthetase activities in tissues from FATP4 null mice. J. Biol. Chem. 280, 11948-11954 (2005).
Hauswirth, W. W. et al. Treatment of leber congenital amaurosis due to RPE65 mutations by ocular subretinal injection of adeno-associated virus gene vector: shortterm results of a phase I trial. Hum. Gene Ther. 19, 979-990 (2008).
Jacobson, S. G. et al. Defining the residual vision in leber congenital amaurosis caused by RPE65 mutations. Invest. Ophthalmol. Vis. Sci. 50, 2368-2375 (2009).
Jacobson, S. G. et al. Human cone photoreceptor dependence on RPE65 isomerase. Proc. Natl. Acad. Sci. U. S. A. 104(38), 15123-15128 (2007).
Jacobson, S. G. et al. Identifying photoreceptors in blind eyes caused by RPE65 mutations: Prerequisite for human gene therapy success. Proc. Natl. Acad. Sci. U. S. A. 102(17), 6177-6182 (2005).
Jacobson, S. G. et al. Improvement and decline in vision with gene therapy in childhood blindness. N. Engl. J. Med. 372, 1920-1926 (2015).
Jacobson, S. G. et al. Photoreceptor layer topography in children with leber congenital amaurosis caused by RPE65 mutations. Invest. Ophthalmol. Vis. Sci. 49, 4573-4577 (2008).
Jakobsson, C. et al. Cone-rod dystrophy caused by a novel homozygous RPE65 mutation in Leber congenital amaurosis. Klin Monbl Augenheilkd 231(4), 405-410 (2014).
Jia, Z. et al. Fatty acid transport protein 4 is the principal very long chain fatty acyl-CoA synthetase in skin fibroblasts. J. Biol. Chem. 282, 20573-20583 (2007).
Jin, M. et al. Role of LRAT on the retinoid isomerase activity and membrane association of Rpe65. J. Biol. Chem. 282 (29), 20915-20924 (2007).
Jin, M. et al. Rpe65 is the retinoid isomerase in bovine retinal pigment epithelium. Cell 122, 449-459 (2005).
Jin, M. et al. The role of interphotoreceptor retinoid-binding protein on the translocation of visual retinoids and function of cone photoreceptors. J. Neurosci. 29, 1486-1495 (2009).
Kim, S. R. et al. Rpe65 Leu450Met variant is associated with reduced levels of the retinal pigment epithelium lipofuscin fluorophores A2E and iso-A2E. Proc. Natl. Acad. Sci. U. S. A. 101(32), 11668-11672 (2004).
Kiser, P. D. et al. Crystal structure of native RPE65, the retinoid isomerase of the visual cycle. Proc. Natl. Acad. Sci. U. S. A. 106(41), 17325-17330 (2009).
Labonte, E. D. et al. Reduced absorption of saturated fatty acids and resistance to diet-induced obesity and diabetes by ezetimibe-treated and Npc1l1−/− mice. Am J Physiol Gastrointest Liver Physiol 295, G776-783 (2008).
Langer, R. New Method of Drug Delivery. Science 249(4976):1527-1533 (1990).
Lee, M. et al. Interphotoreceptor Retinoid-Binding Protein Mitigates Cellular Oxidative Stress and Mitochondrial Dysfunction Induced by All-trans-Retinal. Invest. Ophthalmol. Vis. Sci. 57, 1553-1562 (2016).
Li, B. et al. Inactivity of human beta, beta-carotene-9', 10'-dioxygenase (BCO2) underlies retinal accumulation of the human macular carotenoid pigment. Proc. Natl. Acad. Sci. U.S.A. 111(28), 10173-10178 (2014).
Li, B. et al. Retinal accumulation of zeaxanthin, lutein, and beta-carotene in mice deficient in carotenoid cleavage enzymes. Exp. Eye Res. 159, 123-131 (2017).
Li, S. et al. Ciliary neurotrophic factor (CNTF) protects retinal cone and rod photoreceptors by suppressing excessive formation of the visual pigments. J. Biol. Chem.293, 15256-15268 (2018).
Li, S. et al. Impacts of deletion and ichthyosis prematurity syndrome associated mutations in fatty acid transport protein 4 on the function of RPE65. FEBS Lett. 594, 540-552 (2020).
Li, S. et al. Rescue of Enzymatic Function for Disease-associated RPE65 Proteins Containing Various Missense Mutations in Non-active Sites. J. Biol. Chem. 289, 18943-18956 (2014).
Li, S. et al. Secretory defect and cytotoxicity: the potential disease mechanisms for the retinitis pigmentosa (RP)-associated interphotoreceptor retinoid-binding protein (IRBP). J. Biol. Chem. 288, 11395-11406 (2013).
Li, S. et al. Temperature-sensitive retinoid isomerase activity of RPE65 mutants associated with Leber Congenital Amaurosis. J Biochem 158, 115-125 (2015).
Li, Y. et al. Mouse model of human RPE65 P25L hypomorph resembles wildtype under normal light rearing but is fully resistant to acute light damage. Hum. Mol. Genet. 10.1093/hmg/ddv178 (2015).
Lieberman et al. (eds). Pharmaceutical dosage form tablets. New York, Marcel Dekker, Inc. (1989).
Lin, J. H. et al. IRE1 signaling affects cell fate during the unfolded protein response. Science 318, 944-949 (2007).
Lorenz, B. et al., A comprehensive clinical and biochemical functional study of a novel RPE65 hypomorphic mutation. Invest. Ophthalmol. Vis. Sci. 49, 5235-5242 (2008).
Maguire, A. M. et al. Safety and efficacy of gene transfer for Leber's congenital amaurosis. N. Engl. J. Med. 358, 2240-2248 (2008).
Milger, K. et al. Cellular uptake of fatty acids driven by the ER-localized acyl-CoA synthetase FATP4. J. Cell Sci. 119 (22), 4678-4688 (2006).
Moiseyev, G. et al. RPE65 is the isomerohydrolase in the retinoid visual cycle. Proc. Natl. Acad. Sci. U. S. A. 102, 12413-12418 (2005).
Morshedian, A. et al. Light-Driven Regeneration of Cone Visual Pigments through a Mechanism Involving RGR Opsin in Muller Glial Cells. Neuron 102(6), 1172-1183 (2019).
Moulson, C. L. et al. Keratinocyte-specific expression of fatty acid transport protein 4 rescues the wrinkle-free phenotype in Slc27a4/Fatp4 mutant mice. J. Biol. Chem. 282(21), 15912-15920 (2007).
Newberry, E. P. et al. Decreased hepatic triglyceride accumulation and altered fatty acid uptake in mice with deletion of the liver fatty acid-binding protein gene. J. Biol. Chem. 278(51), 51664-51672 (2003).
Philp, A. R. et al. Predicting the pathogenicity of RPE65 mutations. Hum. Mutat. 30(8), 1183-1188 (2009).
Punzo, C. et al. Stimulation of the insulin/mTOR pathway delays cone death in a mouse model of retinitis pigmentosa. Nat. Neurosci. 12, 44-52 (2009).
Redmond, T. M. et al. Mutation of key residues of RPE65 abolishes its enzymatic role as isomerohydrolase in the visual cycle. Proc. Natl. Acad. Sci. U. S. A. 102, 13658-13663 (2005).
Redmond, T.M. et al. Rpe65 is necessary for production of 11-cis-vitamin A in the retinal visual cycle. Nat. Genet. 20, 344-351 (1998).
Remington's Pharmaceutical Sciences, Mack Publishing Company, Easton, Pennsylvania, 17th edition, 1985.
Rohrer, B. et al. Cone opsin mislocalization in Rpe65−/− mice: a defect that can be corrected by 11-cis retinal. Invest. Ophthalmol. Vis. Sci. 46, 3876-3882 (2005).
Saliba, R. S. et al. The cellular fate of mutant rhodopsin: quality control, degradation and aggresome formation. J. Cell Sci. 115, 2907-2918 (2002).
Samardzija, M. et al. In conditions of limited chromophore supply rods entrap 11-cisretinal leading to loss of cone function and cell death. Hum. Mol. Genet. 18(7), 1266-1275 (2009).
Samardzija, M. et al. R91W mutation in Rpe65 leads to milder early-onset retinal dystrophy due to the generation of low levels of 11-cis-retinal. Hum. Mol. Genet. 17(2), 281-292 (2008).
Sato, K. et al. M-opsin protein degradation is inhibited by MG-132 in Rpe65(−)/(−) retinal explant culture. Mol. Vis. 18, 1516-1525 (2012).

(56) References Cited

OTHER PUBLICATIONS

Sato, K. et al. Receptor interacting protein kinase-mediated necrosis contributes to cone and rod photoreceptor degeneration in the retina lacking interphotoreceptor retinoid binding protein. J. Neurosci. 33(44), 17458-17468 (2013).
Saudek, Ch. D. et al. A preliminary trial of the programmable implantable medication system for insulin delivery. N. Engl. J. Med. 321(9):574-9 (1989).
Schmitz-Valckenberg, S. et al. Correlation between the area of increased autofluorescence surrounding geographic atrophy and disease progression in patients with AMD. Invest. Ophthalmol. Vis. Sci. 47, 2648-2654 (2006).
Sefton, M. V. Implantable Pumps. CRC Crit. Ref. Biomed. Eng. 14(3):201-240 (1987).
Shyam, R. et al. RPE65 has an additional function as the lutein to meso-zeaxanthin isomerase in the vertebrate eye. Proc. Natl. Acad. Sci. U. S. A. 114, 10882-10887 (2017).
Szel, A. et al. Unique topographic separation of two spectral classes of cones in the mouse retina. J. Comp. Neurol. 325, 327-342 (1992).
Weng, J. et al. Insights into the function of Rim protein in photoreceptors and etiology of Stargardt's disease from the phenotype in abcr knockout mice. Cell 98(1), 13-23 (1999).
Wenzel, A. et al. The Rpe65 Leu450Met variation increases retinal resistance against light-induced degeneration by slowing rhodopsin regeneration. J. Neurosci. 21, 53-58 (2001).
Won, J. et al. Mouse model resources for vision research. J Ophthalmol, vol. 2011, art. 391384, 13 pages (2011).
Wright, C. B. et al. Complementation test of Rpe65 knockout and tvrm148. Invest. Ophthalmol. Vis. Sci. 54, 5111-5122 (2013).
Xiong, W. et al. AAV cis-regulatory sequences are correlated with ocular toxicity. Proc. Natl. Acad. Sci. U. S. A. 116 (12), 5785-5794 (2019).
Zhang, H. et al. Trafficking of membrane-associated proteins to cone photoreceptor outer segments requires the chromophore 11-cis-retinal. J. Neurosci. 28, 4008-4014 (2008).
Zhang, J. et al. Photic generation of 11-cis-retinal in bovine retinal pigment epithelium. J. Biol. Chem. 294(50), 19137-19154 (2019).
Zhang, T. et al. Cone opsin determines the time course of cone photoreceptor degeneration in Leber congenital amaurosis. Proc. Natl. Acad. Sci. U. S. A. 108(21), 8879-8884 (2011).
Zhou, Z. et al. A cellular assay distinguishes normal and mutant TIGR/myocilin protein. Hum. Mol. Genet. 8(12), 2221-2228 (1999).
Znoiko, S. L. et al. Downregulation of cone-specific gene expression and degeneration of cone photoreceptors in the Rpe65−/− mouse at early ages. Invest. Ophthalmol. Vis. Sci. 46, 1473-1479 (2005).

* cited by examiner

I Number of S-cones in 4-month inferior section

| genotype | mean ± SD | n |
|---|---|---|
| WT | 283 ± 11 | 3 |
| KI | 15 ± 5 | 5 |
| KI;Fatp4+/- | 46 ± 8 | 3 |
| KI;Fatp4-/- | 114 ± 12 | 4 |

K Number of S-cones in 6-month-old inferior retinal section

| genotype | mean ± SD | n | fold of KI |
|---|---|---|---|
| KI | 4 ± 2 | 4 | 1 |
| KI;Fatp4+/- | 18 ± 4 | 3 | 4.5 |
| KI;Fatp4-/- | 54 ± 7 | 4 | 13.5 |
| WT | 269 ± 13 | 3 | 67.3 |

| age | genotype | all-*trans*-RAL# | 11-*cis*-ROL | all-*trans*-ROL | retinyl ester# |
|---|---|---|---|---|---|
| 6-week | WT | 37.4 ± 20.2 | 7.7 ± 1.9 | 5.1 ± 0.5 | 50.3 ± 13.6 |
| | KI | 2.1 ± 0.8* | N.D. | 7.9 ± 1.4 | 804 ± 144** |
| | KI;*Fatp4*$^{-/-}$ | 3.2 ± 1.4* | N.D. | 7.5 ± 0.8 | 899 ± 252** |
| 12-week | WT | 29.3 ± 9.1 | 8.95 ± 0.7 | 6.2 ± 1.1 | 72.3 ± 19.2 |
| | KI | 2.3 ± 1.0 | N.D. | 10.7 ± 1.9 | 1564 ± 288*** |
| | KI;*Fatp4*$^{-/-}$ | 2.9 ± 1.0 | N.D. | 10.1 ± 1.9 | 1683 ± 310*** |

All-*trans*-RAL, the cytotoxic retinoid, and retinyl esters are slightly increased in KI;*Fatp4*$^{-/-}$ mice, as compared to age-matched KI mice. However, there are no statistically significant differences between KI and KI;*Fatp4*$^{-/-}$ groups (* $P > 0.1$,  $P > 0.4$, * > 0.8). All data are presented as mean ± SD ($n = 5 \sim 6$).

N.D., not detectable.

Figure 8

METHODS OF TREATMENT

This application is a National Stage Entry of PCT Application No. PCT/US2021/056284, filed on Oct. 22, 2021, which is an International Application which claims priority from U.S. Provisional Patent Application No. 63/104,383, filed on Oct. 22, 2020, and U.S. Provisional Patent Application No. 63/138,177, filed on Jan. 15, 2021, the contents of each of which are incorporated herein by reference in their entireties.

GOVERNMENT INTERESTS

This invention was made with government support under R01 EY028572 awarded by the National Institutes of Health. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to compositions and methods for treating the visual cycle as well as the survival and function of cones and rods in patients with retinal degeneration.

BACKGROUND OF THE INVENTION

Mutations in the RPE65 isomerase gene are associated with LCA, for which there is no effective therapy alleviating progressive retinal degeneration in affected patients.

SUMMARY OF THE INVENTION

The invention provides compositions and methods for treating patients that have RPE65 mutations. For example, embodiments of the invention comprise compositions and methods for preserving color vision in patients with RPE65 mutations.

In one aspect, the invention provides a method for treating or preventing retinal degenerative disease in a subject. In embodiments, the method comprises administering to the subject an effective amount of a composition comprising an antilipemic agent.

In another aspect, the invention provides a method of treating a missense mutation disease in a subject, the method comprising administering to the subject an effective amount of a composition comprising an antilipemic agent.

In an aspect, the invention comprises a method of treating mutation-associated retinal dystrophy, the method comprising administering to the subject an effective amount of a composition comprising an antilipemic agent.

In embodiments, of any of the various methods disclosed herein, the disease or dystrophy comprises RPE65 mutation-associated retinal dystrophy, Leber congenital amaurosis (LCA), autosomal recessive retinitis pigmentosa (ARRP), early-onset severe rod-cone dystrophy, or autosomal dominant retinitis pigmentosa.

In another aspect, the invention provides a method of decreasing fatty acid transport protein 4 (FATP4) expression in a subject, the method comprising administering to the subject an effective amount of a composition comprising an antilipemic agent.

In one aspect, the invention comprises a method of preventing loss of phototransduction in a subject, the method comprising administering to the subject an effective amount of a composition comprising an antilipemic agent.

Another aspect includes a method of increasing the synthesis of cis-retinals in a subject, the method comprising administering to the subject an effective amount of a composition comprising an antilipemic agent. In embodiments, the cis-retinals comprise 11-cis-retinal or 9-cis-retinal.

Yet another aspect includes a method of alleviating cone degeneration or color vision loss in patients with RPE65 mutations, the method comprising administering to the subject an effective amount of a composition comprising an antilipemic agent.

In one aspect, the invention comprises a method of decreasing the photoreceptor degeneration or death in a subject, the method comprising administering to the subject an effective amount of a composition comprising an antilipemic agent.

In various aspects, the invention comprises a method of preserving visual cycle rate in a subject, the method comprising administering to the subject an effective amount of a composition comprising an antilipemic agent.

In embodiments of the various aspects disclosed herein, the antilipemic agent comprises ezetimibe.

In certain embodiments, the composition further comprises 4-phenylbutyrate or a gene therapy agent. The gene therapy agent can comprise AAV-RPE65 or voretigene naparvovec-rzyl.

In one aspect, the invention comprises a pharmaceutical composition for treatment of a retinal degenerative disease comprising an effective amount of an antilipemic agent and a therapeutically acceptable carrier. In embodiments, the retinal degenerative disease comprises RPE65 mutation-associated retinal dystrophy, Leber congenital amaurosis, autosomal recessive retinitis pigmentosa, early-onset severe rod-cone dystrophy, or autosomal dominant retinitis pigmentosa. The antilipemic agent can comprise ezetimibe. In certain embodiments, the composition further comprises an effective amount of a 4-phenylbutyrate or a gene therapy agent. The gene therapy agent can comprise AAV-RPE65 or voretigene naparvovec-rzyl.

Other objects and advantages of this invention will become readily apparent from the ensuing description.

BRIEF DESCRIPTION OF THE FIGURES

FIG. 8 shows retinoid contents in dark-adapted mouse eyes (pmol/eye).

DETAILED DESCRIPTION OF THE INVENTION

Figure 1:
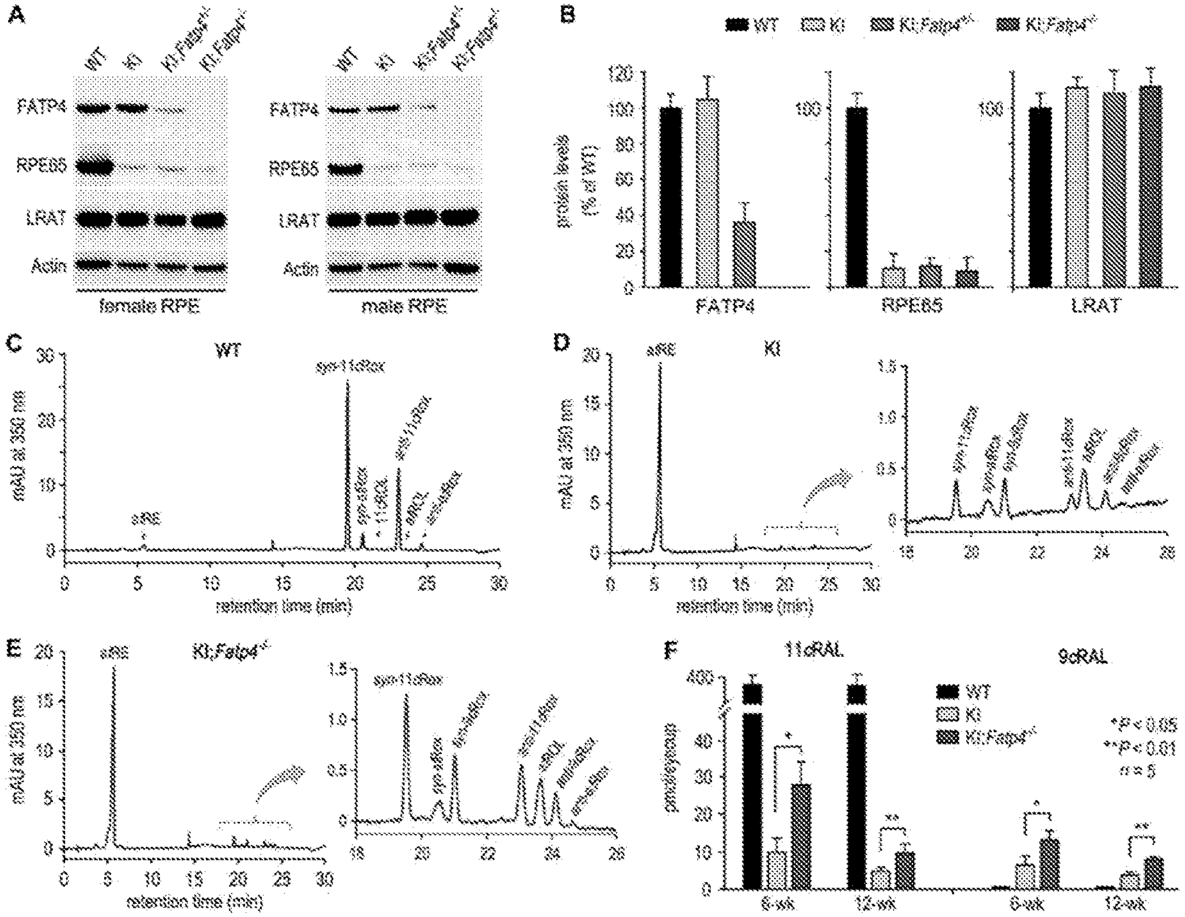
FIG. 1 shows the deletion of FATP4 increased chromophore synthesis in R91W knock-in (KI) mice. (A) Immunoblot analysis of FATP4, RPE65, and LRAT in the mouse RPE with the indicated genotypes. Beta actin was detected as a loading control. (B) Relative expression levels of FATP4, RPE65, and LRAT in the mutant mouse RPE were normalized by actin levels and shown as percent of each protein level in WT mice. (C-E) Representative HPLC chromatograms of ocular retinoids extracted from dark-adapted WT (C), KI (D), and KI;Fatp4$^{-/-}$ (E) mice. The marked peaks are all-trans retinyl esters (atRE), syn-11-cis retinal oxime (syn-11cRox), syn-alltrans retinal oxime (synatRox), 11-cis retinol (11cROL), anti-11-cis retinal oxime (anti-11cRox), all-trans retinol (atROL), anti-all-trans retinal oxime (anti-atRox), syn-9-cis retinal oxime (syn-9cRox), and anti-9-cis retinal oxime (anti-9cRox). (F) Amounts of 11-cis and 9-cis retinals in dark-adapted eyes of 6-week- and 12-week-old WT, KI and KI;Fatp4$^{-/-}$ mice are measured by HPLC analysis.

Mutations in the RPE65 isomerase gene are associated with LCA, for which there is no effective therapy alleviating progressive retinal degeneration in affected patients. Here, we show that FATP4-deficiency markedly increases synthesis of 11-cis- and 9-cis-retinals, improving solubility, stability, and trafficking of cone opsins in the Rpe65 R91W knock-in (KI) mouse model of Leber congenital amaurosis (LCA).

The FDA has approved the first gene therapy targeting a disease caused by mutations of RPE65: LUXTURNA™ (voretigene neparvovec-rzyl; Spark Therapeutics, Inc., Philadelphia, PA). Voretigene neparvovec-rzyl delivers a copy of the RPE65 gene to the retina for treatment of RPE65 mutation-associated retinal dystrophy.

Aspects of the invention are drawn to treating the visual cycle as well as the survival and function of cones and rods in patients with RPE65 mutations.

Aspects of the invention are drawn to a method of treating, ameliorating, and/or preventing retinal degenerative diseases. Aspects of the invention are drawn towards a method of administering an antilipemic agent, either alone or in combination with gene therapy, to treat, ameliorate, or prevent retinal degenerative disease. In an embodiment, the antilipemic agent comprises Ezetimibe. In an embodiment, the gene therapy comprises Voretigene neparvovec-rzyl. In an embodiment, the retinal degenerative disease comprises Leber congenital amaurosis (LCA), autosomal recessive retinitis pigmentosa (ARRP), early-onset severe rod-cone dystrophy, and autosomal dominant retinitis pigmentosa.

Detailed descriptions of one or more embodiments are provided herein. It is to be understood, however, that the invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification can mean "one," but it is also consistent with the meaning of "one or more," "at least one," and "one or more than one" unless such interpretation is nonsensical in context.

Wherever any of the phrases "for example," "such as," "including" and the like are used herein, the phrase "and without limitation" is understood to follow unless explicitly stated otherwise. Similarly, "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the term "administering" can refer to introducing a substance, such as an antilipemic agent alone or in combination with gene therapy, into a subject. Any route of administration can be utilized including, for example, intranasal, topical, oral, parenteral, intravitreal, intraocular, ocular, subretinal, intrathecal, intravenous, subcutaneous, transcutaneous, intracutaneous, intracranial and the like administration. In embodiments, "administering" can also refer to providing a therapeutically effective amount of a formulation or pharmaceutical composition to a subject. The formulation or pharmaceutical compound can be administered alone, but can be administered with other compounds, excipients, fillers, binders, carriers or other vehicles selected based upon, for example, the chosen route of administration and standard pharmaceutical practice. Administration can be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; other proteins and peptides; synthetic polymers; microspheres; or nanoparticles.

The term "administration" can refer to introducing a composition described herein into a subject. Non-limiting examples of routes of administration of the composition comprise topical administration, oral administration, or intranasal administration. However, any route of administration, such as intravenous, subcutaneous, peritoneal, intra-arterial, inhalation, vaginal, rectal, introduction into the cerebrospinal fluid, intravascular either veins or arteries, or instillation into body compartments can be used.

As used herein, "treatment" and "treating" can refer to the management and care of a subject for the purpose of combating a condition, disease or disorder, such as retinal degenerative disorder, in any manner in which one or more of the symptoms of a disease or disorder are ameliorated or otherwise beneficially altered. The term can include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" can refer to the management and care of a patient for the purpose of hindering the development of the condition, disease or disorder, and includes the administration of the active compounds to prevent or reduce the risk of the onset of symptoms or complications.

The term "subject" or "patient" can refer to any organism to which aspects of the invention can be administered, e.g., for experimental, diagnostic, prophylactic, and/or therapeutic purposes. For example, subjects to which compounds of the disclosure can be administered include animals, such as mammals. Non-limiting examples of mammals include primates, such as humans. For veterinary applications, a wide variety of subjects will be suitable, e.g., livestock such as cattle, sheep, goats, cows, swine, and the like; poultry such as chickens, ducks, geese, turkeys, and the like; and domesticated animals for example pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" can refer to a subject noted above or another organism that is alive. The term "living subject" can refer to the entire subject or organism and not just a part excised (e.g., a liver or other organ) from the living subject.

As used herein, the term "retinal degenerative disease" can refer to a disease associated with retinal deterioration or degeneration. For example, the retinal degeneration can comprise a progressive neurological disorder caused by genetic mutations, environmental damage, and/or pathologic damage. For example, the retinal degenerative disease can be caused by apoptosis of retinal neural cells or adjacent supporting tissue. In embodiments, the deterioration or degeneration can be the result of a missense mutation disease, mutation-associated retinal dystrophy, RPE65 mutation-associated retinal dystrophy, Leber congenital amaurosis (LCA), autosomal recessive retinitis pigmentosa (ARRP), early-onset severe rod-cone dystrophy, or autosomal dominant retinitis pigmentosa.

In embodiments, the disease or disorder can be caused by a mutation in the RPE65 gene. RPE65 refers to retinal pigment epithelium-specific 65 kDa protein. As used herein, RPE65 can also be referred to as retinoid isomerohydrolase. RPE65 is a component of the vitamin A visual cycle of the retina and supplies the 11-cis retinal chromophore of the photoreceptor's opsin visual pigments. Although RPE65 is a member of the carotenoid cleavage oxygenase superfamily, RPE65's function involves the concerted O-alkyl ester cleavage of its all-trans retinyl ester substrate and all-trans to 11-cis double bond isomerization of the retinyl moiety. As such, RPE65 performs the enzymatic isomerization step in the synthesis of 11-cis retinal. Mutations in the RPE65 gene are associated with early-onset severe blinding disorders such as Leber congenital (see RPE65 retinoid isomerohydrolase RPE65. Bethesda (MD): National Library of Medicine (US), National Center for Biotechnology Information; [accessed 18 Oct. 2021]; available from ncbi.nlm.nih.gov/gene/6121).

Aspects of the invention are drawn towards treating and/or preventing retinal degeneration in a subject. The invention can include method of treating and/or preventing mutation-associated retinal dystrophy in a subject. As used herein, "mutation-associated retinal dystrophy" can refer to any retinal condition comprising retinal degeneration that is caused by a genetic mutation. Aspects of the invention are drawn towards treating and/or preventing missense mutation disease in a subject. As used herein, the term "missense mutation disease" can comprise any disease or disorder caused by a missense mutation. As used herein, the term "missense mutation" can refer to a point mutation in which a single nucleotide change results in a code that codes for a different amino acid. Aspects of the invention are drawn towards treating and/or preventing a disease or disorder caused by a hypomorphic mutation. As used herein, the term "hypomorphic" refers to a mutation that causes a partial loss of gene function.

Aspects of the invention are drawn towards treating and/or preventing RPE65 mutation-associated retinal dystrophy, Leber congenital amaurosis (LCA), autosomal recessive retinitis pigmentosa (ARRP), early-onset severe rod-cone dystrophy, or autosomal dominant retinitis pigmentosa. In embodiments, treating or preventing RPE65 mutation-associated retinal dystrophy, Leber congenital amaurosis (LCA), autosomal recessive retinitis pigmentosa (ARRP), early-onset severe rod-cone dystrophy, or autosomal dominant retinitis pigmentosa comprise administering an antilipemic agent. For example, the antilipemic agent comprises ezetimibe.

Aspects of the invention are drawn towards mitigating progressive loss of sight in patients. In embodiments, mitigating progressive loss of sight comprises improving visual cycle, improving survival, or improving function of cones, rods, or a combination thereof in patients with missense mutations. In embodiments, administering an antilipemic agent can contribute to mitigating progressive loss of sight in a patient. For example, the antilipemic agent comprises ezetimibe.

As used herein, the term "visual cycle" can refer to the biochemical process by which a light-sensitive isomer of vitamin A is continually recycled. As used herein, the term "phototransduction" can refer to the process by which photoreceptors initiate vision by converting photons to electrical activity. For example, photoreceptors can refer to neuroepithelial cells found in the retina that are capable of phototransduction. For example, two types of photoreceptors in the retina are rods and cones. 3 types of cones comprise L-cones (also referred to as red cones), M-cones (also referred to as green cones), and S-cones (also referred to as blue cones. The rods and cones contain pigment-protein compounds referred to as a photopigment. In rods the photopigment is rhodopsin. Rhodopsin can be covalently bound to 11-cis-retinal in rod photoreceptor cells. When a photon is absorbed, the 11-cis-retinal can then isomerize to the all-trans retinal which can enable rhodopsin to activate transducing.

Aspects of the invention are drawn towards treating or preventing color vision loss.

Electroretinogram (ERG) can refer to a diagnostic test which measures electrical activity of the retina in response to a light stimulus. ERG can be an objective measure of retinal function that can be recorded under physiological conditions. In embodiments, ERG can be used to provide diagnostic information, monitor the progression of retinal diseases and disorders, or a combination thereof. ERG can be used to determine the effectiveness of any of the various compositions disclosed herein. In embodiments, ERG is used to measure phototransduction, visual cycle rate, color vision loss, or a combination thereof. In certain embodiments, visual cycle rate is measured via scotopic ERG combined with dark adaptation rate. Color vision loss can be assayed via flicker ERG, photopic ERG, or a combination thereof. In embodiments, ERG values from subjects who have not been diagnosed with a retinal degenerative disease are within the following values: ERG 0.5-Hz blue light≥about 100 V; ERG 0.5-Hz white light≥about 350 μV; ERG 30-Hz white flicker≥about 50 μV. In certain embodiments, ERG data from patients diagnosed with retinal degenerative disease comprise the following: ERG 0.5-Hz blue light<about 100 μV; ERG 0.5-Hz white light<about 350 μV; ERG 30-Hz white flicker<about 50 μV. Additional examples of ERG values from healthy subjects and patients can be found in Lorenz et al., A comprehensive clinical and biochemical functional study of a novel RPE65 hypomorphic mutation. Invest. Ophthalmol. Vis. Sci. 49, 5235-5242 (2008).

Optical coherence tomography (OCT) can refer to a non-invasive imaging test that uses light waves to capture cross-sectional images of a retina. OCT can be used to distinguish layers of the retina, map and measure thickness, inform treatment decisions, provide diagnostic information, monitor disease progression, or a combination thereof. OCT can be used to determine the effectiveness of any of the various compositions disclosed herein. In embodiments, OCT can be used to quantify photoreceptor degeneration or photoreceptor death. OCT can be used to quantify cone degeneration. In embodiments, subjects who have not been diagnosed with a retinal degenerative disease have a peak cone density in the fovea of about 200,000 cells/mm$^2$ as measured by OCT. Subjects who have not been diagnosed with a retinal degenerative disease can have a foveal outer nuclear layer thickness of about 100 μm as measured by OCT. In embodiments, patients diagnosed with retinal degenerative disease have a peak cone density in the fovea of less than about 200,000 cells/mm$^2$ as measured by OCT. Patients diagnosed with a retinal degenerative disease can have a foveal outer nuclear layer thickness of less than about 100 μm as measured by OCT. Additional examples of OCT values from healthy subjects and patients diagnosed with a retinal degenerative disease can be found in Lorenz et al., 2008.

Aspects of the invention are drawn towards a method of decreasing fatty acid transport protein 4 (FATP4) expression in a subject. In certain embodiments, the method comprises administering an effective amount of a composition comprising an antilipemic agent. Aspects of the invention are drawn towards using FATP4 as a therapeutic target for treating and/or preventing a retinal degenerative disease in a subject. As used herein, the term "therapeutic target" can refer to a gene or gene product that, upon modulation of its activity, provides a therapeutic effect. For example, the therapeutic effect can comprise increasing visual cycle rate, decreasing photoreceptor degeneration or death, or alleviating cone degeneration and color vision loss in a subject.

Aspects of the invention are drawn towards administering an antilipemic agent to a subject in need thereof. As used herein, the term "antilipemic" refers to a substance used to reduce serum lip levels in a patient. Antilipemic agents can refer to substances that lower serum low density lipoprotein (LDL) cholesterol levels. Antilipemic agents can comprises substances that lower triglyceride levels in a patient. Antilipemic agents can include substances that raise high density lipoprotein cholesterol levels. In embodiments, antilipemic agents include pharmaceuticals that treat or prevent hypercholesterolemia, hyperlipidemia, or a combination thereof. Exemplary antilipemic agents comprise cholesterol absorption inhibitors. In one embodiment, the antilipemic agent comprises ezetimibe.

In embodiments, the antilipemic agent can be administered with an additional active agent. For example, the additional active agent can comprise a gene therapy agent. The additional active agent can comprise 4-phenylbutyrate. As used herein, the term "gene therapy agent" can refer to an agent that provides genetic modifications to produce a therapeutic effect. In embodiments, the gene therapy agent can comprise AAV-RPE65, voretigene naparvovec-rzyl, or a combination thereof.

As used herein, the terms "therapeutically effect amount," "therapeutically effective dose" and "effective amount" can be used interchangeably. The term "therapeutically effective amount" as used herein can refer to that amount of a composition or a pharmaceutical composition being administered that will relieve, to some extent, one or more of the symptoms of the disease or condition being treated, and/or that amount that will prevent, to some extent, one or more of the symptoms of the condition or disease that the subject being treated has or is at risk of developing. A therapeutically effective dose can depend upon a number of factors known to those of ordinary skill in the art. The dosage can vary depending upon known factors such as the pharmacodynamic characteristics of the active ingredient and its mode and route of administration; time of administration of active ingredient; identity, size, condition, age, sex, health and weight of the subject or sample being treated; nature and extent of symptoms; kind of concurrent treatment, frequency of treatment and the effect desired; and rate of excretion. These amounts can be readily determined by the skilled artisan.

In embodiments a therapeutically effective amount comprises an amount of any of the various compositions disclosed herein that is sufficient to alleviate progression of retinal degeneration in an affected patient. The phrase "alleviate progression" can refer to cessation of retinal degeneration, slowing the progression of retinal degeneration, or reversing retinal degeneration in a patient.

In embodiments, a therapeutically effective amount comprise an amount of any of the various compositions disclosed herein that is sufficient to stop, slow, or reverse the effects of retinal degeneration in an affected patient. In one embodiment, a therapeutically effective amount comprise an amount of any of the various compositions disclosed herein that is sufficient to prevent further loss of visual phototransduction in a patient suffering from a retinal degenerative disease. In embodiments, visual phototransduction, is measured via ERG.

A therapeutically effective amount can comprise an amount of any of the various compositions disclosed herein that is sufficient to alleviate photoreceptor degeneration or photoreceptor death. In embodiments, a therapeutically effective amount comprises an amount of any of the various compositions disclosed herein that is sufficient to alleviate cone degeneration. The term "alleviate cone degeneration" can refer to cessation of cone degeneration, slowing the progression of cone degeneration, or reversing cone degeneration in a patient. In embodiments alleviation of cone degeneration is measured via Optical Coherence Tomography (OCT). In one embodiment, OCT data obtained from a pre-treatment time point is compared with OCT data obtained from a treatment time point following a period of treatment of a patient with any of the various compositions disclosed herein. OCT data can be compared at multiple timepoints during the treatment period. In embodiments, a therapeutically effective amount is an amount of any of the various compositions disclosed herein that is sufficient to stop progression of photoreceptor degeneration, slow progression of photoreceptor degeneration, or reverse photoreceptor degeneration in a patient during the treatment period. In one embodiment, a cessation of photoreceptor degeneration occurs if OCT data from the treatment time point shows a photoreceptor population that is similar or identical to that of the pre-treatment time point, Cessation of photo receptor degeneration can occur when there is less than about 5% variance form the pre-treatment timepoint to the treatment timepoint. In certain embodiments, a variance of up to about 1%, about 2%, about 3%, about 4%, or about 5% indicates cessation of photoreceptor degeneration. Slowing of photoreceptor degeneration can occur if the photoreceptor population at the treatment timepoint is up to about 80% of the photoreceptor population observed at the pre-treatment timepoint. In embodiments, slowing of photoreceptor degermation occurs when the photoreceptor population is about 80%, about 85%, about 90%, or about 95% of the photoreceptor population. Reversal of photoreceptor degeneration in a patient can occur when OCT data from the treatment timepoint shows a photoreceptor population that is greater than that of the pre-treatment timepoint. Reversal of photoreceptor degeneration in a patient can occur when OCT data obtained from the patient is similar to that of an subject who is not suffering from a retinal degenerative disease.

In various embodiments, the period of treatment is at least one week. The treatment period can be up to about 20 years. In embodiment, the treatment period comprises 1 week, 2 weeks, 3, weeks, 4 weeks, 5 weeks, 6 weeks, 7 weeks, 8 weeks, 9 weeks, 10 weeks, 11 weeks, or 12 weeks. The treatment period can be about 1 month, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, about 21 months, about 22 months, or about 24 months. In certain embodiments, the treatment can continue for the lifetime of the patient following diagnosis of a retinal degenerative disease.

In embodiments, a therapeutically effective amount comprises an amount of any of the various compositions disclosed herein that is sufficient to alleviate color vision loss. Color vision loss can be assayed via photopic ERG.

A therapeutically effective amount can comprise an amount of any of the various compositions disclosed herein that is sufficient to increase visual cycle rate in a patient. In certain embodiments, a therapeutically effective amount comprises an amount of any of the various compositions disclosed herein that is sufficient to preserve visual cycle rate in a patient suffering from retinal degeneration. In embodiments, the visual cycle rate is measured via dark adaptation rate, scotopic ERG, or a combination thereof.

A therapeutically effective amount can comprise an amount of any of the various compositions disclosed herein that is sufficient to increase synthesis of 11-cisretinals, 9-cis retinals, or combination thereof in a patient.

Suitable excipient vehicles for the composition or pharmaceutical composition are, for example, water, saline, dextrose, glycerol, ethanol, or the like, and combinations thereof. In addition, the vehicle can contain minor amounts of auxiliary substances such as wetting or emulsifying agents, antioxidants or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pennsylvania, 17th edition, 1985. The composition or formulation to be administered will, in any event, contain a quantity of the composition or pharmaceutical composition adequate to achieve the desired state in the subject being treated.

Compositions described herein can include those that comprise a sustained release or controlled release matrix. In addition, embodiments of the present disclosure can be used in conjunction with other treatments that use sustained-release formulations. As used herein, a sustained-release matrix is a matrix made of materials, for example polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix. In another embodiment, the pharmaceutical composition of the present disclosure (as well as combination compositions) can be delivered in a controlled release system. For example, the composition or pharmaceutical composition can be administered using intravenous infusion, an implantable osmotic pump, a transdermal patch, liposomes, or other modes of administration. In one embodiment, a pump can be used (Sefton (1987). CRC Crit. Ref. Biomed. Eng. 14:201; Buchwald et al. (1980). Surgery 88:507; Saudek et al. (1989). N. Engl. J. Med. 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). Science 249:1527-1533.

In another embodiment, the compositions or pharmaceutical compositions (as well as combination compositions separately or together) can be part of a delayed-release formulation. Delayed-release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, M D, 2000, and "Pharmaceutical dosage forms and drug delivery systems", 6th Edition, Ansel et al., (Media, PA: Williams and Wilkins, 1995). These references provide information on excipients, materials, equipment, and process for preparing tablets and capsules and delayed release dosage forms of tablets, capsules, and granules. These references provide information on carriers, materials, equipment, and process for preparing tablets and capsules and delayed release dosage forms of tablets, capsules, and granules.

Embodiments of the composition or pharmaceutical composition can be administered to a subject in one or more doses. Those of skill will readily appreciate that dose levels can vary as a function of the specific the composition or pharmaceutical composition administered, the severity of the symptoms and the susceptibility of the subject to side effects. Dosages for a given compound are readily determinable by those of skill in the art by a variety of means. In embodiments, the dose comprises a therapeutically effective amount.

In an embodiment, multiple doses of the composition or pharmaceutical composition are administered. The frequency of administration of the composition or pharmaceutical composition can vary depending on any of a variety of factors, e.g., severity of the symptoms, and the like. For example, in an embodiment, the composition or pharmaceutical composition can be administered once per month, twice per month, three times per month, every other week (qow), once per week (qw), twice per week (biw), three times per week (tiw), four times per week, five times per week, six times per week, every other day (qod), daily (qd), twice a day (qid), three times a day (tid), or four times a day. As discussed above, in an embodiment, the composition or pharmaceutical composition is administered 1 to 4 times a day over a 1 to 10-day time period.

The duration of administration of the composition or pharmaceutical composition analogue, e.g., the period of time over which the composition or pharmaceutical composition is administered, can vary, depending on any of a variety of factors, e.g., patient response, etc. For example, the composition or pharmaceutical composition in combination or separately, can be administered over a period of time of about one day to one week, about one day to two weeks.

As used herein, "pharmaceutically acceptable derivatives" of a compound can include salts, esters, enol ethers, enol esters, acetals, ketals, orthoesters, hemiacetals, hemiketals, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs.

A "pharmaceutically acceptable excipient," "pharmaceutically acceptable diluent," "pharmaceutically acceptable carrier," or "pharmaceutically acceptable adjuvant" can refer to an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used herein can include one and more such excipients, diluents, carriers, and adjuvants.

The phrase "pharmaceutical composition" or a "pharmaceutical formulation" can refer to a composition or pharmaceutical composition suitable for administration to a subject, such as a mammal, especially a human and that can refer to the combination of an active agent(s), or ingredient with a pharmaceutically acceptable carrier or excipient, making the composition suitable for diagnostic, therapeutic, or preventive use in vitro, in vivo, or ex vivo. A "pharmaceutical composition" can be sterile and can be free of contaminants that can elicit an undesirable response within the subject (e.g., the compound(s) in the pharmaceutical composition is pharmaceutical grade). Pharmaceutical compositions can be designed for administration to subjects or patients in need thereof via a number of different routes of administration including oral, intranasal, topical, intravenous, buccal, rectal, parenteral, intraperitoneal, intradermal, intracheal, intramuscular, subcutaneous, by stent-eluting devices, catheters-eluting devices, intravascular balloons, inhalational and the like.

In embodiments, the pharmaceutical composition can comprise a therapeutically effective amount of an antilipemic agent and a therapeutically effective amount of one or more additional active agents. As used herein, the term "additional active agent" can refer to a biologically active substance that is administered in addition to another active agent. For example, the additional active agent can be a gene therapy agent. For example, the gene therapy agent can be AAV-REP65 or voretigene naparvovec-rzyl. For example, the active agent can be 4-phenylbutyrate. In embodiments, the pharmaceutical composition can comprise an antilipemic agent, a gene therapy agent, a 4-phenylbutyrate, or a combination thereof. For example, the antilipemic agent is ezetimibe or an analog thereof. In embodiments, the antilipemic agent can be a 2-azetidinone cholesterol absorption inhibitor.

As used herein, the term "analog" can refer to a molecule which possesses similar or identical function as another molecule. For example, an analog can refer to an agent that is structurally similar to another but differs in composition (e.g., the replacement of one atom by an atom from a different element or the presence or replacement of a functional group).

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Example 1—Therapeutics to Mitigate Progressive Loss of Sight by Improving Visual Cycle, Survival and Function of Cones and Rods in Patients with Missense Mutations Fatty acid transport protein 4 (FATP4), a transmembrane protein in the endoplasmic reticulum (ER), is a negative regulator of the ER-associated RPE65 isomerase necessary for recycling 11-cis-retinal, the light sensitive chromophore of both rod and cone opsin visual pigments. Here we discovered that FATP4-deficiency in the retinal pigment epithelium (RPE) results in 2.8-fold and 1.7-fold increase of 11-cis- and 9-cis-retinals, respectively, improving dark-adaptation rates as well as survival and function of rods in the Rpe65 R91W knock-in (KI) mouse model of Leber congenital amaurosis (LCA). Degradation of S-opsin in the proteasomes, but not in the lysosomes, was remarkably reduced in the KI mouse retinas lacking FATP4. FATP4-deficiency also rescued S-opsin trafficking and M-opsin solubility in the KI retinas. The number of S-cones in the inferior retinas of 4- or 6-month-old KI; $Fatp4^{-/-}$ mice was 7.6- or 13.5-fold greater than those in age-matched KI mice. Degeneration rates of S- and M-cones are negatively correlated with expression levels of FATP4 in the RPE of the KI, KI;$Fatp4^{+/-}$, and KI;$Fatp4^{-/-}$ mice. Moreover, the visual function of S- and M-cones is markedly preserved in the KI; $Fatp4^{-/-}$ mice, displaying an inverse correlation with the FATP4 expression levels in the RPE of the three mutant lines. Our discovery establishes FATP4 as a therapeutic target to improve the visual cycle as well as survival and function of cones and rods in patients with RPE65 mutations and other missense mutations.

Reduction of RATP4 in the RPE improved survival and function of S- and M-cones in KI; $Fatp4^{+/-}$ mice (PNAS 2020) indicating that pharmacological suppression of FATP4 expression can alleviate cone degeneration and color vision loss in patients with RPE65 mutations.

As described herein, Ezetimibe, an inhibitor of Niemann-Pick C1-like 1 cholesterol influx transporter can elicit the effects. Ezetimibe is a U.S. Food and Drug Administration-approved drug as an add-on to dietary measures to lower plasma cholesterol. In animal studies, Ezetimibe markedly reduced expression of FATP4 in intestinal cells (E. D. Labonte et al., *Am J Physiol Gastrointest Liver Physiol* 295, G776-783 2008); M. Naples et al., *Am J Physiol Gastrointest Liver Physiol* 302, G1043-1052 (2012)). Without wishing to be bound by theory, Ezetimibe is a safe and low-cost therapeutic for alleviating retinal degeneration and vision loss in patients with RPE65 mutations. Combination applications of Ezetimibe, 4-phenylbutyrate, and AAV-RPE65 can be an effective intervention for long-term preservation of vision in the patients.

We will further expand the therapeutic application spectrum of our findings, by validating whether FATP4-deficiency and Ezetimibe treatment are effective at mitigating the progressive death of photoreceptors in animal models with RPE65-null or other missense mutations.

Example 2

Example 2—Inverse Correlation Between Fatty Acid Transport Protein 4 and Vision in Leber Congenital Amaurosis Associated with RPE65 Mutation Abstract Fatty acid transport protein 4 (FATP4), a transmembrane protein in the endoplasmic reticulum (ER), is a recently identified negative regulator of the ER-associated RPE65 isomerase necessary for recycling 11-cis-retinal, the light sensitive chromophore of both rod and cone opsin visual pigments. The role of FATP4 in the disease progression of retinal dystrophies associated with RPE65 mutations is completely unknown. Here we show that FATP4-deficiency in the retinal pigment epithelium (RPE) results in 2.8-fold and 1.7-fold increase of 11-cis- and 9-cis-retinals, respectively, improving dark-adaptation rates as well as survival and function of rods in the Rpe65 R91W knock-in (KI) mouse model of Leber congenital amaurosis (LCA). Degradation of S-opsin in the proteasomes, but not in the lysosomes, was remarkably reduced in the KI mouse retinas lacking FATP4. FATP4-deficiency also significantly rescued S-opsin trafficking and M-opsin solubility in the KI retinas. The number of S-cones in the inferior retinas of 4- or 6-month-old KI;$Fatp4^{-/-}$ mice was 7.6- or 13.5-fold greater than those in age-matched KI mice. Degeneration rates of S- and M-cones are negatively correlated with expression levels of FATP4 in the RPE of the KI, KI;$Fatp4^{+/-}$, and KI;$Fatp4^{-/-}$ mice. Moreover, the visual function of S and M-cones is markedly preserved in the KI;$Fatp4^{-/-}$ mice, displaying an inverse correlation with the FATP4 expression levels in the RPE of the three mutant lines. These findings establish FATP4 as a therapeutic target to improve the visual cycle as well as survival and function of cones and rods in patients with RPE65 mutations.

Mutations in the RPE65 isomerase are associated with LCA, for which there is no effective therapy alleviating progressive retinal degeneration in affected patients. Here, we show that FATP4-deficiency increases synthesis of 11-cis- and 9-cis-retinals, improving solubility, stability, and trafficking of cone opsins in the Rpe65 R91W knock-in (KI) mouse model of LCA. Numbers of S-cones in the inferior retinas of 4- or 6-month-old KI;$Fatp4^{-/-}$ mice were 7.6- or 13.5-fold greater than those in KI mice. Survival rates and function of both S- and M-cones are negatively correlated with expression levels of FATP4 in the RPE of KI, KI;$Fatp4^{+/-}$, and KI;$Fatp4^{-/-}$ mice. These findings establish FATP4 as a therapeutic target to preserve color vision in patients with RPE65 mutations.

Introduction

RPE65 is a key retinoid isomerase (1-4) in the visual cycle responsible for recycling 11-cis-retinal (11cRAL), which functions not only as a molecular switch for initiating the phototransduction in response to light stimuli, but also as a chaperone for normal trafficking of cone opsins to the outer segments of cones (5, 6). RPE65 is also the isomerase responsible for the production of meso-zeaxanthin (7), one of the three macular pigments in the human retina that function as potent antioxidants and light screening pigments to protect the macula (8). Expression levels and activities of RPE65 are positively correlated with an increase in both retinal susceptibility to light-induced degeneration (9, 10) and the accumulation rates of the visual cycle-derived cytotoxic bisretinoids, the major autofluorescent components of lipofuscin implicated in Stargardt disease and geographic atrophy of age-related macular degeneration (11-13).

Mutations in the RPE65 gene cause vision impairment and retinal degeneration in affected patients, canines, and mice. In humans, more than 100 DNA variants in the RPE65 gene are reported as pathogenic mutations causing retinal degenerative diseases (Global Variome shared LOVD: database.lovd.nl/shared/genes/RPE65). Although night blindness is the first significant symptom in most patients with RPE65 mutations, in vivo microscopy of the fovea demonstrated that many patients exhibited severe cone degeneration at very early ages (14,15). The role of RPE65 in maintaining human cone photoreceptor health and vision is also supported by its abundant expression and higher activity in the macaque central RPE layer localized to the cone-rich area (16).

There is no approved effective treatment available for diseases caused by RPE65 mutations. In clinical trials, subretinally injected AAV-RPE65 has improved vision in some patients (17-20). However, subsequent studies showed that the gene therapy could not stop progressive retinal degeneration in patients (21-23). In addition, more than half of the subjects injected with a higher dose of AAV-RPE65 developed various degrees of intraocular inflammation (23). AAV cis-regulatory sequences are associated with toxic effects on the RPE and microglial cells (24). Lower dose of AAV-RPE65 can reduce the side effects but it will limit the beneficial outcome of this very high-cost therapy because only a small population of RPE cells will express the exogenous RPE65 (17). These studies indicate the need for alternative interventions and improved gene therapy to prevent progressive retinal degeneration in patients.

A recent study showed that systemic administration of 4-phenylbutyrate (PBA) could partially rescue the function of mutated RPE65, thereby improving the preservation of photoreceptors and vision in a mouse model of LCA (25). This study indicates that rescuing the intrinsic function of mutated RPE65 has the potential to mitigate retinal degeneration in patients with RPE65 mutations. Studies in cultured cells have shown that RPE65 mutants can be rescued by chemical and physical treatments (26, 27). One of approach that can rescue RPE65 mutants, and thereby enhance the efficacy of the gene therapy and PBA-treatment, is to modulate endogenous regulators of RPE65.

Through screening of RPE cDNA libraries, we have identified FATP4 as a negative regulator of RPE65 (28). FATP4 is a transmembrane protein with an ER-localization domain (29). Among the six members of the FATP family, FATP4 is the most abundant FATP in the RPE. It has fatty acyl-CoA synthetase activity with specificity toward saturated and monounsaturated very long-chain fatty acids. Activation of C24:0, but not C16:0, fatty acid was reduced in the FATP4 null mouse cells (30, 31). In an in vitro assay for RPE65 isomerase, lignoceroyl (C24:0)-CoA inhibited the synthesis of 11-cis-retinol (11cROL), whereas palmitoyl (C16:0)-CoA promoted the synthesis of 11cROL (28). In addition, FATP4 has been shown to interact with RPE65 and inhibits 11cROL synthesis catalyzed by RPE65 (32). Consistent with these studies, the retinoid isomerase activity and the visual cycle rates are increased in a mouse line lacking FATP4 in the RPE (28).

In the study, we validated the role and mechanisms of FATP4 function in regulating the visual cycle as well as survival and function of rod and cone photoreceptors in pathological conditions caused by hypomorphic R91W RPE65, the most common RPE65 mutant linked to LCA. The R91W mutation has been shown to cause early degeneration of cones in affected patients and animal models (33, 34). We found that FATP4 is a promising therapeutic target to preserve cones and vision in patients with RPE65 mutation.

Results

Deletion of FATP4 Increased Synthesis of 11cRAL and 9-Cis-Retinal (9cRAL) in the R91W Knock-In (KI) Mouse Model of LCA To investigate the role of FATP4 in disease progress of the KI mouse, we generated KI mouse lines with a $Fatp4^{-/-}$ or $Fatp4^{+/-}$ genotype. Immunoblot analysis of RPE showed that RPE65 expression levels in KI, KI;$Fatp4^{+/-}$, and KI;$Fatp4^{-/-}$ mice were approximately 10% of wild-type (WT) RPE65 (FIG. 1, panels A and B). This observation is consistent with the previous study showing rapid degradation of R91W RPE65 through the ubiquitin-proteasomal pathway (25) and indicates that FATP4 had no significant effect on the stability of the mutant RPE65. Expression levels of lecithin:retinol acyltransferase (LRAT), which synthesizes the substrate of RPE65, in all mutant lines were similar to that in the WT mouse RPE. FATP4 expression was reduced by 60% in the KI;$Fatp4^{+/-}$ RPE, as compared to the WT mouse RPE, and was not detectable in the KI;$Fatp4^{-/-}$ mouse RPE (FIG. 1, panels A and B).

We then analyzed ocular retinoids in the mice. To stabilize the highly reactive retinals, we converted 11cRAL and all-trans-retinal into syn- and anti-retinaloxime isomers using hydroxylamine (35). High-performance liquid chromatography (HPLC) data showed that the amounts of 11cRAL and 9cRAL, a functional iso-chromophore (36), were increased 2.8-fold and 1.7-fold, respectively, in the dark-adapted KI;$Fatp4^{-/-}$ mice (FIG. 1, panel F), whereas the amounts of all trans-retinal, all-trans-retinol and all-trans-retinyl esters in the KI;$Fatp4^{-/-}$ mice were not significantly changed, as compared to those in age-matched KI mice (FIG. 1, panels C-F and FIG. 8).

Figure 2:
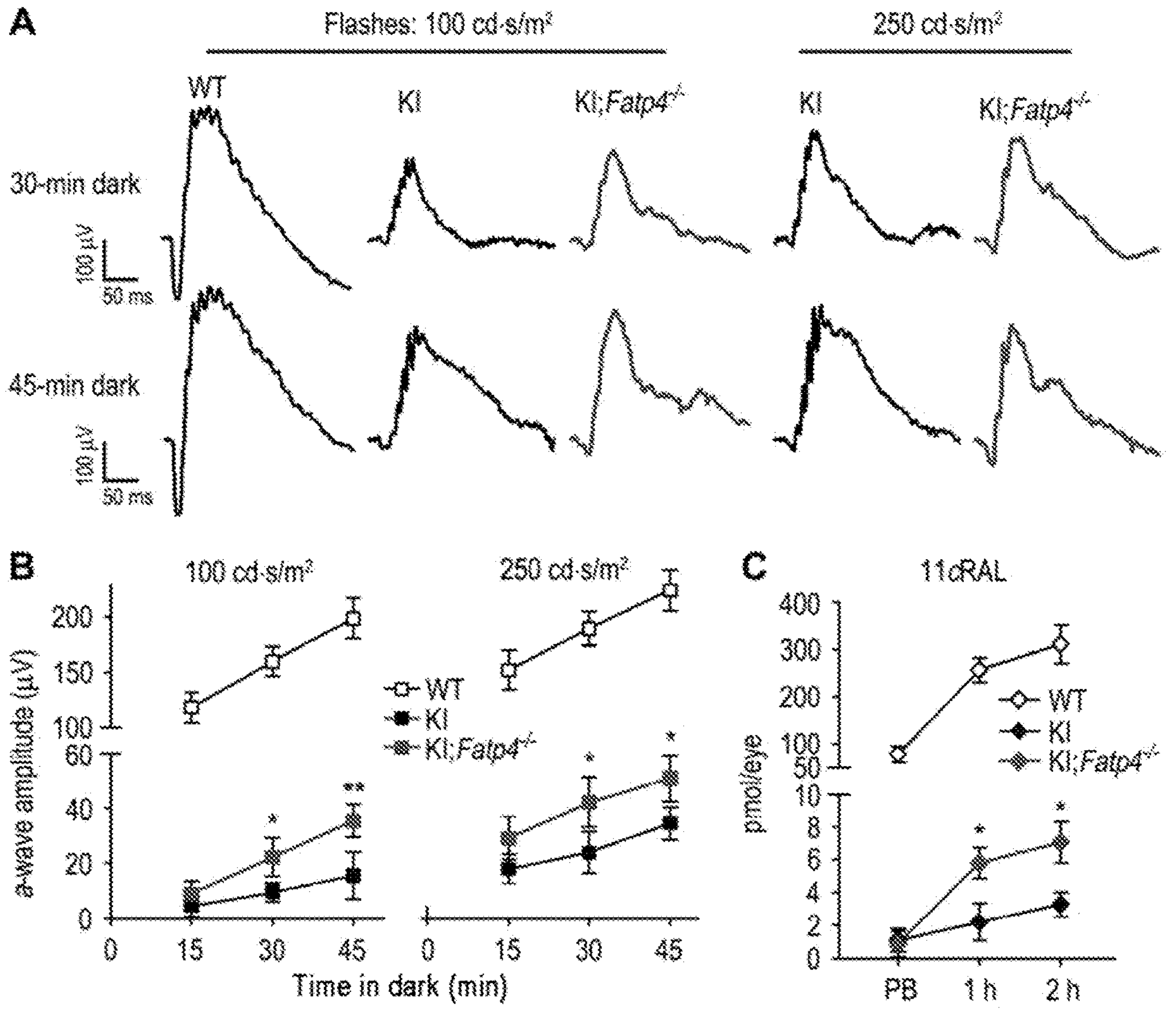
FIG. 2 shows accelerated recovery of rod light sensitivity and chromophore synthesis in KI;Fatp4$^{-/-}$ mice. (A) Representative scotopic ERG responses of WT, KI, and KI;Fatp4$^{-/-}$ mice to 100 or 250 cd·s/m$^2$ flashes. The mice were kept in darkness for 30-min or 45-min after photobleaching the visual pigments. (B) Amplitudes of scotopic ERG a-waves evoked by 100 cd·s/m$^2$ or 250 cd·s/m$^2$ flashes in WT, KI, and KI;Fatp4$^{-/-}$ mice kept in darkness for the indicated times after photobleaching the visual pigments. (C) Amounts of 11-cis-retinal (11cRAL) in WT, KI, and KI;Fatp4$^{-/-}$ mouse eyes are measured at the indicated conditions: immediately after photobleaching (PB), dark-adapted for 1 h or 2 h after photobleaching. Asterisks indicate significant differences between KI and KI;Fatp4$^{-/-}$ mice (*P<0.04, **P<0.005). Error bars show SD (n=4~6).

FATP4-Deficiency Accelerated Recovery of Rod Light Sensitivity and 11cRAL Synthesis in the KI Mice To know whether the increased 11cRAL in the KI;Fatp4−/− mice (FIG. 1) is associated with an improvement of the visual cycle, we compared recovery rates of rod light sensitivities in KI and KI;$Fatp4^{-/-}$ mice. After photobleaching rhodopsin, we put mice in the dark for different times. We then recorded scotopic electroretinograms (ERG) of the mice. KI and KI;$Fatp4^{-/-}$ mice kept in darkness for 15 min exhibited similar amplitudes of a-waves in response to a series of light flashes (50~250 cd·s/m2). However, a-wave amplitudes of KI;$Fatp4^{-/-}$ mice dark-adapted for 30-min or 45-min were significantly greater than those of the KI mice under the same light conditions (FIG. 2, panels A and B). We measured recovery of 11cRAL synthesis in the mice adapted to dark for different times. Since KI and KI;$Fatp4^{-/-}$ mice contain small amounts of the visual chromophores, we kept mice in darkness for 1 or 2 hours after photobleaching the visual pigments. As shown in FIG. 2, panel C, the amounts of 11cRAL in KI;$Fatp4^{-/-}$ mice kept in darkness for 1 and 2 hours were greater than those in KI mice at the same dark-adaptation conditions.

Alleviation of Rod Degeneration in the KI Mice Lacking FATP4

Figure 3:
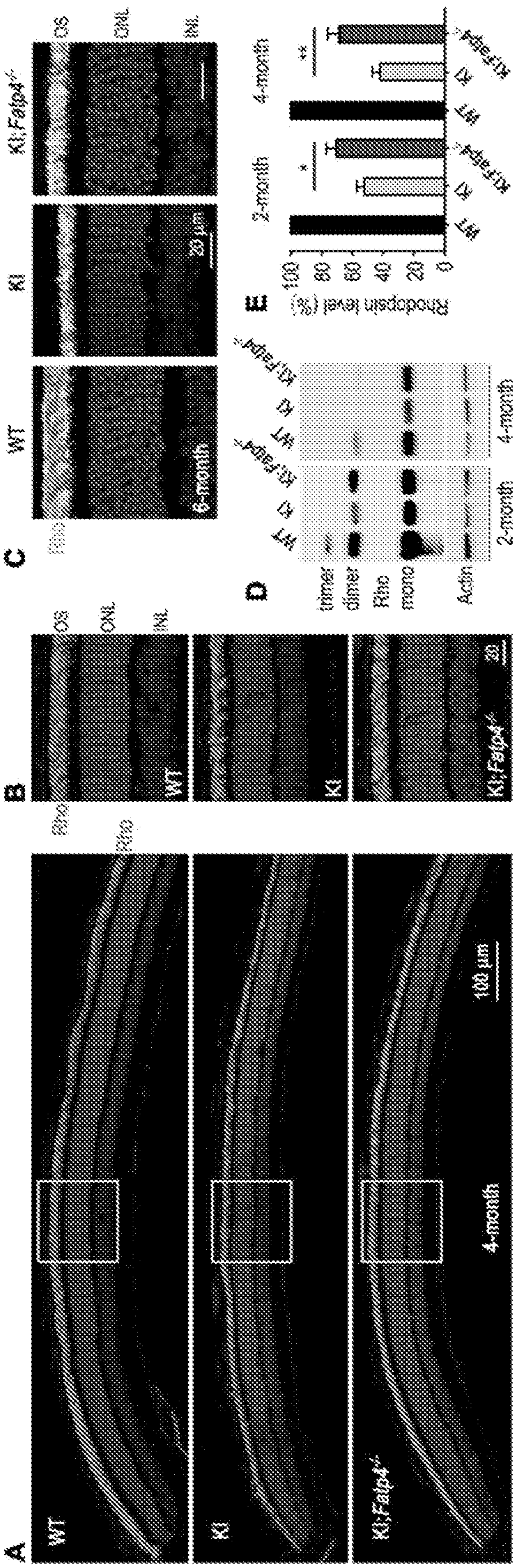
FIG. 3 shows FATP4-deficiency mitigated degeneration of rods in KI mice. (A) Immunostaining of rhodopsin (Rho, red) in the superior retinas of 4-month-old WT, KI, and KI;Fatp4$^{-/-}$ mice. Nuclei were counterstained with DAPI (blue). (B) Higher magnification images of the areas of rectangles shown in (A). OS, outer segments; ONL, outer nuclear layer; INL, inner nuclear layer. (C) Representative immunostaining of Rho (green) in the central areas of 6-month-old WT, KI, and KI;Fatp4$^{-/-}$ mouse superior retinas. (D) Immunoblot analysis of Rho in the retinas of 2- and 4-month-old WT, KI, and KI;Fatp4$^{-/-}$ mice. (E) Relative expression levels of Rho in the KI and KI;Fatp4$^{-/-}$ retinas were normalized by actin levels and shown as percent of Rho levels in the WT retinas. Asterisks indicate significant differences between KI and KI;Fatp4$^{-/-}$ mice (*P<0.03, **P<0.004). Error bars show SD (n=3).

The KI mice exhibit a disorganization of photoreceptor outer segments (OS) as early as 4 weeks of age, and this OS disorganization/degeneration advances with aging (37). To know whether FATP4-deficiency attenuates rod degeneration in KI mice, we performed immunocytochemistry of rhodopsin in WT, KI, and KI;$Fatp4^{-/-}$ mice. As shown in FIG. 3, panels A-C, the lengths of rod OS in 4- and 6-month-old KI;Fatp4$^{-/-}$ mice are longer than those in age-matched KI mice. The thickness of the outer nuclear layer (ONL) was also preserved in 6-month-old KI;Fatp4−/− mice as compared to that of 6-month-old KI mice (FIG. 3, panel C). Consistent with these observations, quantitative immunoblot analysis showed that expression levels of rhodopsin were increased by ~40% or ~70%, respectively, in 2- or 4-month-old KI;Fatp4$^{-/-}$ mice, as compared to age-matched KI mice (FIG. 3, panel D and E), while expression levels of rhodopsin in 2- and 4-month-old KI mice were approximately 50% or 40% of those in age-matched WT mice (FIG. 3, panel D and E).

Figure 4:
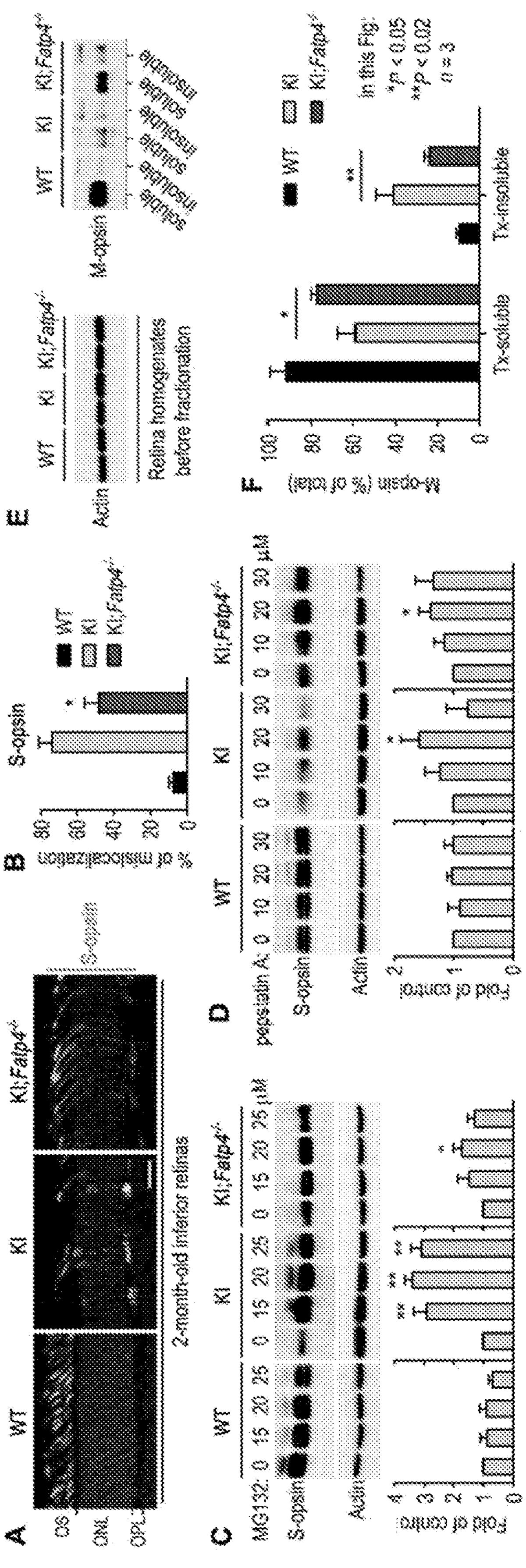
FIG. 4 shows improved trafficking, stability and solubility of cone opsins in KI;Fatp4$^{-/-}$ mice. (A) S-opsin (green) immunohistochemistry in WT, KI, and KI;Fatp4$^{-/-}$ inferior retinas. OS, outer segments; ONL, Outer nuclear layer; OPL, outer plexiform layer. Scale bar, 20-μm. (B) Percentage of Sopsin mislocalization estimated by dividing S-opsin immunofluorescence in the OPL by the sum of immunofluorescence in the OPL and OS. Note the decrease in S-opsin mislocalization in KI;Fatp4$^{-/-}$ mice. (C,D) Immunoblot analysis of S-opsin in retinal explants treated with the indicated concentrations of MG132 (C) or pepstatin A (D). DMSO was used in the MG132 and pepstatin A null controls. Histograms show relative immunoblot intensities of S-opsin in MG132-treated and pepstatin A-treated retinas versus DMSO-treated controls. (E) Representative immunoblot analysis of M-opsin in Triton X-100 (Tx)-soluble and -insoluble retinal fractions separated by ultracentrifugation (right panel). Left panel shows immunoblots of actin in the retinal homogenates before ultracentrifugation. (F) Percentages of Tx-soluble and -insoluble Mopsin in WT, KI, and KI;Fatp4$^{-/-}$ mice are estimated from the immunoblot intensities in (E).

Improved Trafficking, Stability and Solubility of Cone Opsins in KI;Fatp4$^{-/-}$ Mice Lack and severe shortage of 11cRAL supply due to RPE65 mutations cause cone opsin mislocalization in animal models (5, 6, 34). Since 11cRAL and 9cRAL are increased in the KI;Fatp4$^{-/-}$ mice, we tested whether S-opsin mislocalization is reduced in the KI;Fatp4$^{-/-}$ retina. Immunohistochemistry of S-opsin showed that mislocalization of S-opsin was reduced in the KI;Fatp4$^{-/-}$ retinas as compared to the KI retinas (FIG. 4, panel A). Quantitative analysis revealed that S-opsin mislocalization was reduced by approximately 40% in the KI;Fatp4$^{-/-}$ mice (FIG. 4, panel B).

As the first step to analyze the mechanisms resulting in reduction of S-opsin mislocalization in the KI;Fatp4$^{-/-}$ cones, we incubated WT and mutant retinas with MG132 (a proteasome inhibitor) or pepstatin A (a lysosome inhibitor) in media of the retinal explants. Immunoblot analysis showed that the amounts of S-opsin in the KI and KI;Fatp4$^{-/-}$ retinas, but not in the WT retinas, were significantly increased by the treatments (FIG. 4, panel C and D). The relative amounts of S-opsin were increased 3-fold or 1.6-fold, respectively, in the KI and KI;Fatp4$^{-/-}$ retinas treated with MG132, as compared to the same genotype retinas treated with DMSO; while the relative amounts of S-opsin in the KI and KI;Fatp4$^{-/-}$ retinas treated with pepstatin A were increased by ~55% or ~43%, respectively, as compared to DMSO-treated retinas (FIG. 4, panel C and D). These results indicate that a large fraction of S-opsin proteins in the KI cones are misfolded and underwent degradation in the proteasomes. Increase in the synthesis of 11cRAL and 9cRAL in KI;Fatp4$^{-/-}$ mice reduced the proteasomal degradation of S-opsin in the cones. The results also indicate that a portion of S-opsin proteins in both KI and KI;Fatp4$^{-/-}$ retinas underwent lysosomal degradation, which could not be reduced by the increased 11cRAL and 9cRAL in the KI;Fatp4$^{-/-}$ retina.

To further confirm whether cone opsins are misfolded in the KI cones, we analyzed solubility of M-opsin. We homogenized retinas in phosphate buffered saline (PBS) containing Triton X-100 detergent and separated opsins into soluble and insoluble fractions by ultracentrifugation. Immunoblot analysis of these fractions showed that more than 90% of M-opsin in the WT retina was included in the soluble fraction whereas only ~58% of M-opsin in the KI retina was distributed to the soluble fraction (FIG. 4, panel E and F). In the KI;Fatp4$^{-/-}$ retina, the soluble M-opsin was increased to ~78% (FIG. 4, panel E and F). Consistent with this result, insoluble M-opsin was significantly reduced in the KI;Fatp4$^{-/-}$ retina, as compared to the KI retina (FIG. 4, panel E and F).

Figure 5:
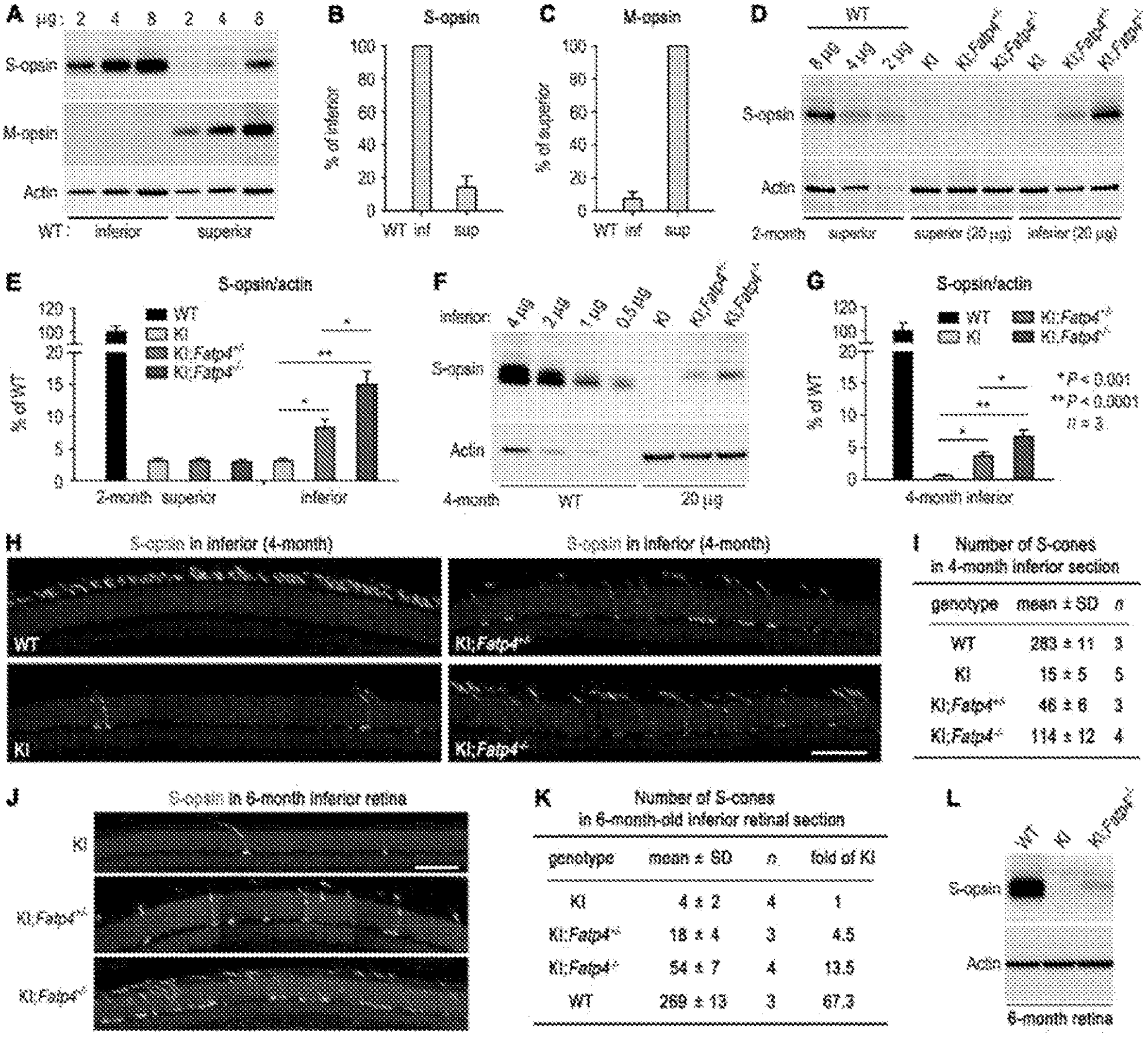
FIG. 5 shows inverse correlation between S-cone degeneration and FATP4 expression in KI mouse models. (A) Immunoblot analysis of S- and M-opsins in the indicated amounts (μg) of retinal homogenates from inferior or superior halves of WT mouse retinas. (B,C) Percentages of Sopsin (B) and M-opsin (C) included in the inferior and superior halves of WT retinas. (D) Immunoblot analysis of S-opsin in the inferior and superior halves of 2-month-old mouse retinas with the indicated genotypes. (E) Relative expression levels of S-opsin in the inferior or superior halves of 2-month-old KI, KI;Fatp4$^{+/-}$, and KI;Fatp4$^{-/-}$ retinas are shown as percent of S-opsin levels in the inferior or superior halves of WT retinas. (F) Immunoblot analysis of S-opsin in the inferior halves of 4-month-old WT, KI, KI;Fatp4$^{+/-}$, and KI;Fatp4$^{-/-}$ mouse retinas. (G) Relative expression levels of S-opsin in the inferior half of 4-month-old KI, KI;Fatp4$^{+/-}$, and KI;Fatp4$^{-/-}$ retinas are shown as percent of S-opsin levels in age-matched WT inferior retinas. (H) Immunostaining of S-opsin in the inferior retinas of 4-month-old WT, KI, KI;Fatp4$^{+/-}$, and KI;Fatp4$^{-/-}$ mice. (1) Numbers of S-cones in the inferior retinas of sections taken from the dorsalventral midline of 4-month-old mouse eyes. (J) Immunostaining of S-opsin in the inferior retinas of 6-month-old with the indicated genotypes. Scale bars denote 100-μm. (K) Comparison of Scone numbers in the inferior retinal sections of 6-month-old mice. (L) Immunoblot analysis of S-opsin in 6-month-old retinas of WT, KI, and KI;Fatp4$^{-/-}$ mice.
Figure 6:
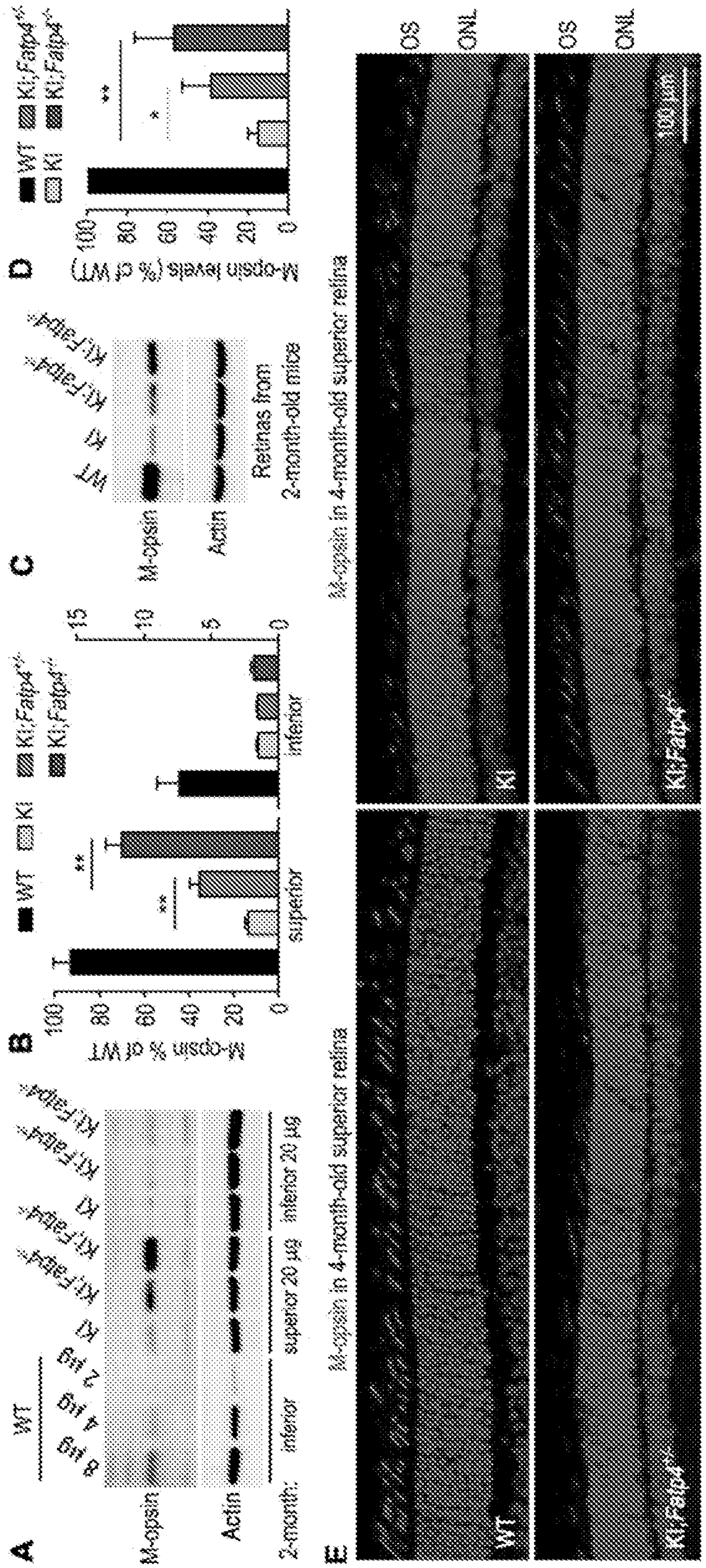
FIG. 6 shows M-cone preservation is negatively correlated with FATP4 expression in KI mouse lines. (A) Immunoblot analysis of M-opsin in the indicated amounts (μg) of retinal homogenates from the inferior or superior halves of WT, KI, KI;Fatp4$^{+/-}$, and KI;Fatp4$^{-/-}$ mice. (B) Expression levels of M-opsin in the superior or inferior halves of 2-month-old KI, KI;Fatp4$^{+/-}$, and KI;Fatp4$^{-/-}$ retinas are normalized with actin levels and shown as percent of M-opsin levels in the WT mouse superior or inferior retinas. (C) Immunoblot analysis of M-opsin in total retinal homogenates of 2-month-old WT, KI, KI;Fatp4$^{+/-}$, and KI;Fatp4$^{-/-}$ mice. (D) Histogram showing percentages of normalized M-opsin immunoblot intensities in the mutant retinas relative to the M-opsin intensities in the WT retinas. (E) Immunostaining of M-opsin in the superior retinas of 4-month old mice with the indicated genotypes.

FATP4 Expression Levels in the RPE are Negatively Correlated with Degeneration Rates of S- and M-Cones in the LCA Mice In the mouse eyes, M-cones are present in the superior half of the retina while the majority of S-cones are present in the inferior half of the retina (38). To increase the detection sensitivity of cone opsins and to accurately assess the degeneration rates of S- and M-cones in the KI and KI;Fatp4$^{-/-}$ mice, we performed quantitative immunoblot analysis using inferior and superior halves of the mouse retinas. Approximately 85% of S-opsin (S-cones) and 92% of M-opsin (Mcones) are present in the inferior or superior half of 2-month-old WT mouse retinas, respectively (FIG. 5A-C). Expression levels of S-opsin in the inferior retinas of 2-month-old KI;Fatp4$^{+/-}$ and KI;Fatp4$^{-/-}$ mice were 2.7-fold or 5-fold higher than that in the inferior retina of age-matched KI mice, respectively (FIG. 5, panel D and E). The differences of S-opsin expression levels in the KI mice and KI mice with Fatp4$^{+/-}$ or Fatp4$^{-/-}$ genotypes were enlarged to approximately 6-fold and 11-fold, respectively, at 4-month of mouse age (FIG. 5, panel F and G). We did not observe a significant increase of S-opsin in the superior retinas of KI;Fatp4$^{+/-}$ and KI;Fatp4$^{-/-}$ mice (FIG. 5, panel D and E), possibly due to almost complete loss of S-cones in the superior retinas that contain a small population of S-cones (FIG. 5, panel A-E). On the other hand, immunoblot analysis showed a significant increase of M-opsin in the superior retinas of KI;Fatp4$^{+/-}$ and KI;Fatp4$^{-/-}$ mice, as compared to age-matched KI mouse superior retinas (FIG. 6, panel A-D).

We also performed immunohistochemistry for S- and M-opsins. The number of S-cones preserved in the inferior retinas of 4-month-old KI;Fatp4$^{+/-}$ and KI;Fatp4$^{-/-}$ mice was 3.1-fold or 7.6-fold greater than those in age-matched KI mouse inferior retinas (FIG. 5, panel H and I). The number of M-opsin positive cells in the superior retinas of 4-month-old KI;Fatp4$^{+/-}$ and KI;Fatp4$^{-/-}$ mice was also greater than those in the superior retinas of KI mice (FIG. 6, panel E).

All of the three mutant lines (KI, KI;Fatp4$^{+/-}$, and KI;Fatp4$^{-/-}$) displayed a progressive degeneration of S-cones with aging. In the KI mice, however, the degeneration rates of S-cones were much faster than those in KI;Fatp4$^{+/-}$ and KI;Fatp4$^{-/-}$. As a result, the number of S-cones preserved in the inferior retinas of 6-month-old KI;Fatp4$^{+/-}$ and KI;Fatp4$^{-/-}$ was approximately 4.5-fold or 13.5-fold greater than those in age-matched KI mouse inferior retinas (FIG. 5, panel J and K). Immunoblot analysis indicated that S-opsin was almost undetectable in 6-month-old KI mouse inferior retinas while KI;Fatp4$^{-/-}$ mouse inferior retinas still contained a significant amount of S-opsin at the same age (FIG. 5, panel L). The results described above indicate that the degrees of S-cone degeneration are negatively correlated with the expression levels of FATP4 in the RPE of the three LCA models at 2, 4 and 6 months of age.

Figure 7:
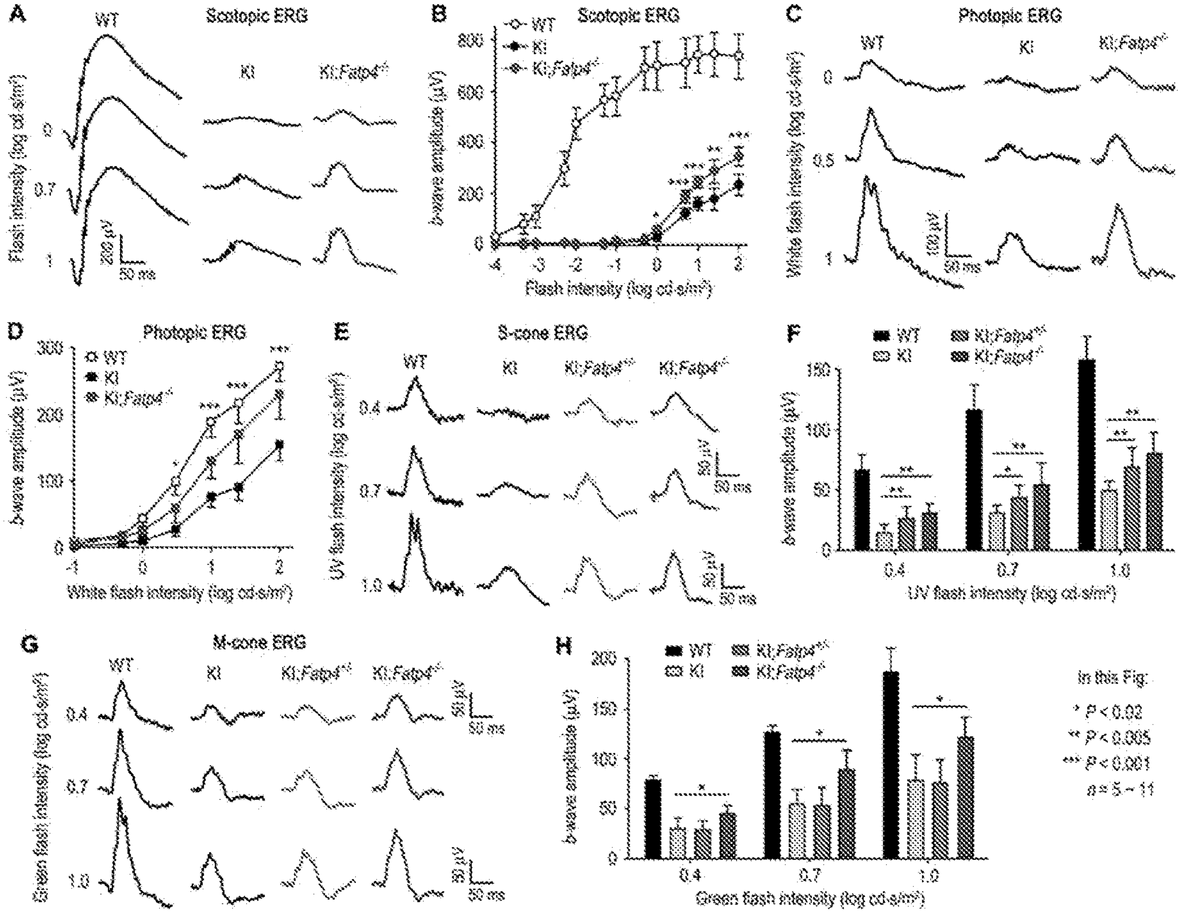
FIG. 7 shows inverse correlation between FATP4 expression and visual function of rods and cones in KI mouse models. (A) Representative scotopic ERG responses of dark-adapted 6-week-old WT, KI, and KI;Fatp4$^{-/-}$ mice to the indicated flashes (0~1 log cd·s/m2). (B) Amplitudes of scotopic ERG b-waves elicited with the indicated flashes in WT, KI, and KI;Fatp4$^{-/-}$ mice. (C) Photopic ERG responses of 3-month-old WT, KI, and KI;Fatp4$^{-/-}$ mice to the indicated flashes of white light under a rod-saturating background light. (D) Amplitudes of photopic ERG b-waves evoked with the indicated light flashes in WT, KI, and KI;Fatp4$^{-/-}$ mice. Asterisks indicate significant differences between KI and KI;Fatp4$^{-/-}$ mice. (E) Representative ERG responses of S-cones in 3-month-old WT, KI, KI;Fatp4$^{+/-}$, and KI;Fatp4$^{-/-}$ mice to 360 nm UV light flashes under a rod saturating background light. (F) Amplitudes of S-cone ERG b-waves evoked with the indicated intensities of UV light flashes in WT, KI, KI;Fatp4$^{+/-}$, and KI;Fatp4$^{-/-}$ mice. (G) Representative ERG responses of M-cones in 3-month-old WT and the indicated mutant mice to the flashes of 530 nm green light. (H) Amplitudes of M-cone ERG b-waves evoked with the indicated intensities of 530 nm light flashes. Asterisks indicate significant differences between KI and KI;Fatp4$^{-/-}$ mice.

Inverse Correlation Between Visual Function and FATP4 Expression in the LCA Mouse Lines To test whether FATP4-deficiency improves the visual function, we recorded scotopic and photopic ERG responses in KI and KI;Fatp4$^{-/-}$ mice. As shown in FIG. 7, panel A-D, photoresponses of both rods and cones in KI;Fatp4$^{-/-}$ mice were greater than those in KI mice. To evaluate the function of S- and M-cones separately, we recorded ERG responses with UV and green lights. Amplitudes of S-cone b-waves evoked by UV flashes were significantly higher in KI;Fatp4$^{+/-}$ and KI;Fatp4$^{-/-}$ mice, as compared to KI mice (FIG. 7, panel E and F); b-wave amplitudes of M-cones in KI;Fatp4$^{-/-}$ mice were also greater than those of the KI mouse M-cones (FIG. 7, panel G and H).

Discussion

In this study, we have studied FATP4 as a new therapeutic target by providing evidence that FATP4-deficiency in the RPE increases the synthesis of 11cRAL and 9cRAL, improving the visual cycle, rod light sensitivity, as well as stability, solubility, and trafficking of cone opsins in mouse models of LCA. We further showed that survival and function of cones are significantly enhanced in KI;Fatp4$^{-/-}$ mice, and are negatively correlated with FATP4 expression levels in the RPE of KI, KI;Fatp4$^{+/-}$, and KI;Fatp4$^{-/-}$ mice. Without wishing to be bound by theory, these findings indicate that pharmacological approaches suppressing FATP4 expression can mitigate cone degeneration and vision loss in patients with RPE65 mutations.

RPE65 uses all-trans retinyl fatty acid esters (atRE) as its substrate to synthesize 11cROL (2). The fatty acid moiety of atRE can be crucial for binding with RPE65 and can facilitate substrate access to the catalytic site located inside a hydrophobic pocket of RPE65 (39). In agreement with these studies, our previous experiments showed that FATP4 competes with RPE65 for the atRE substrate of RPE65 (28). In addition, our recent study indicates that interaction between FATP4 and RPE65 also contributes to inhibition of the RPE65-catalyzed synthesis of 11cROL (32). These studies indicate that enhancement of all-trans to 11-cis isomerization catalyzed by R91W RPE65 is the main mechanism for rescuing the visual cycle in the KI mice lacking FATP4. Although the RPE retinal G protein-coupled receptor (RGR) also catalyzes the all-trans to 11-cis isomerization to make 11cRAL (40-42), the following data indicate that FATP4-deficiency promoted the RPE65-catalyzed isomerization rather than the RGR-mediated isomerization: 1) amplitudes of scotopic ERG a-waves in 30 or 45 min dark adapted KI;Fatp4$^{-/-}$ mice were much higher than those in KI mice under the same dark adaptation conditions (FIG. 2, panel A and B), and 2) the amount of 11cRAL synthesized during one hour dark adaptation of KI;Fatp4$^{-/-}$ mice was greater than that in KI mice under the same conditions (FIG. 2, panel C). These results indicate that FATP4-deficiency promoted 11cRAL synthesis in a light-independent mechanism, while RGR-mediated synthesis of 11cRAL requires light stimuli (40-42).

Similar to the early cone degeneration phenotypes in dogs and mice with Rpe65 mutations (34, 43, 44), patients with some RPE65 mutations (including R91W mutation) exhibit a significant loss of cones at very early ages (14, 15, 33, 45). Mislocalization of cone opsins can contribute to the early cone degeneration in the Rpe65$^{-/-}$ and KI mice (5, 34). In this study, we observed that FATP4-deficiency in the RPE reduced mislocalization of S-opsin in the KI mice (FIG. 4, panel A and B). This mitigation of S-opsin mislocalization can be due to an increase in correct folding of S-opsin rather than correcting a trafficking defect of the opsin. Visual chromophores of 11cRAL and 9cRAL have been shown to function as chaperones for folding of mutated opsin (46). These data indicate that 11cRAL and 9cRAL increase in the KI;Fatp4$^{-/-}$ retina promoted the native folding of cone opsins, which in turn improved the normal trafficking and stability of S-opsin in the KI;Fatp4$^{-/-}$ cones (FIG. 4, panel A-D).

To know whether M-opsin is also misfolded in the KI cones, we analyzed M-opsin solubility in Triton X-100 (Tx), a non-ionic detergent that has been used to distinguish normal and misfolded mutant proteins (47, 48). We observed that most of M-opsin proteins in the WT retina were soluble in the Tx-containing homogenate whereas only ~60% of M-opsin proteins in the KI retina were soluble under the same detergent conditions (FIG. 4, panel E and F). Soluble fraction of M-opsin proteins were increased to ~80% in the KI;Fatp4$^{-/-}$ retina, while insoluble Mopsin were reduced in the KI;Fatp4$^{-/-}$ retina, as compared to the KI retina (FIG. 4, panel E and F). Without wishing to be bound by theory, these results indicate that increased synthesis of the 11cRAL and 9cRAL chromophores promoted the normal folding of M-opsin, thereby improving the solubility of M-opsin in the KI;Fatp4$^{-/-}$ retina.

We observed that S-opsin in the KI and KI;Fatp4$^{-/-}$ cones underwent degradation via both the proteasomal and the lysosomal pathways. However, MG132 and pepstatin A displayed different effects on the inhibition of S-opsin degradation in the KI and KI;Fatp4$^{-/-}$ retinal explants. As compared to DMSO-treated controls, S-opsin was increased 3-fold or 1.6-fold in the KI and KI;Fatp4$^{-/-}$ retinal explants treated with MG132, (FIG. 4, panel C), while in the presence of pepstatin A, S-opsin was increased by ~55% or ~43% in the KI and KI;Fatp4$^{-/-}$ retinal explants, respectively (FIG. 4, panel D). These data indicate that the misfolded S-opsin that undergoes the proteasomal degradation in the KI retina is rescued in the KI;Fatp4$^{-/-}$ retina, whereas the misfolded S-opsin that undergoes lysosomal degradation is barely rescued in the KI;Fatp4$^{-/-}$ retina. These differences can reflect two different phases of misfolded S-opsin proteins in the mutant cones. In the early phase of misfolding, S-opsin can be refolded by the chromophores that are increased in the KI;Fatp4$^{-/-}$ mice; therefore, proteasomal degradation of S-opsin is reduced and MG132 has a smaller effect on increasing S-opsin stability in KI;Fatp4$^{-/-}$ retinas compared to KI retinas (FIG. 4, panel C). In the late phase of misfolding, S-opsin proteins formed aggregates that undergo lysosomal degradation via the autophagy-mediated autolysosome pathway. The aggregates of misfolded S-opsin cannot be refolded by 11cRAL and 9cRAL; therefore, pepstatin A exhibited a similar effect on S-opsin stability in both KI and KI;Fatp4$^{-/-}$ retinas (FIG. 4, panel D). These interpretations are in agreement with the following observations: 1) transmembrane proteins that fail to assume their native structure are subject to ER-associated degradation via the ubiquitin-proteasomal pathway (49), 2) M-opsin undergoes rapid degradation in the proteasomes of Rpe65$^{-/-}$ cones (50), whereas ubiquitinated S-opsin accumulates in the Lrat$^{-/-}$ cones (51), and 3) autophagy is activated during cone death in animal models of retinal dystrophies (52).

Compared to the 4-phenylbutyrate treatment that elevated 11cRAL by 96% in the KI mice (25), FATP4-deficiency exhibited a higher effect on increasing 11cRAL synthesis in the KI mice. In the KI;Fatp4$^{-/-}$ mice, 11cRAL was increased 2.8-fold as compared to KI mice. FATP4-deficiency also promoted the synthesis of 9cRAL in the KI mice. Since 9cRAL is increased in Rpe65$^{-/-}$ mice too (36), 9cRAL can be increased via a RPE65-independent pathway in the KI;Fatp4$^{-/-}$ mice. Nevertheless, due to the rescue of 11cRAL and 9cRAL synthesis, survival and function of cones dramatically improved in the KI;Fatp4$^{-/-}$ mice. Mice lack the macula pigments (58, 59) and, therefore, the preservation of cones in the KI;Fatp4$^{-/-}$ mice can be not related to the meso-zeaxanthin synthesis catalyzed by RPE65. Importantly, we found that partial reduction of FATP4 in the RPE improved survival and function of S- and M-cones in KI;Fatp4$^{+/-}$ mice (FIGS. 5-7). Without wishing to be bound by theory, these findings indicate that pharmacological suppression of FATP4 expression can alleviate cone degeneration and color vision loss in patients with RPE65 mutations.

Ezetimibe is an inhibitor of Niemann-Pick C1-like 1 cholesterol influx transporter and a U.S. Food and Drug Administration-approved medication used as an add-on to dietary measures to lower plasma cholesterol. In animal studies, Ezetimibe markedly reduced expression of FATP4 in intestinal cells (60, 61), indicating that Ezetimibe is a safe and low-cost therapeutic for alleviating retinal degeneration and vision loss in patients with RPE65 mutations. Combination application of Ezetimibe, 4-phenylbutyrate, and AAV-RPE65 can be an effective intervention for long-term preservation of vision in the patients. To expand the therapeutic application spectrum of our findings, we will validate whether FATP4-deficiency and Ezetimibe treatment are effective at mitigating the progressive death of photoreceptors in animal models with RPE65-null or other missense mutations.

Materials and Methods

Animals The $Fatp4^{-/-}$;lvl-$Fatp4^{tg/+}$ (shown as $Fatp4^{-/-}$ in this study) and R91W knock-in (KI) mice have been described previously (25, 28, 37, 62). Both of these mutant mouse lines have been backcrossed with WT 129S2/Sv strain to generate $Fatp4^{-/-}$ and KI mice homozygous for the Leu450 allele of the Rpe65 gene. We crossed these new KI and new $Fatp4^{-/-}$ mice, then intercrossed the heterozygous offspring to yield KI;$Fatp4^{-/-}$ and KI;$Fatp4^{+/-}$ mice. All animal experiments were performed in accordance with the Association for Research of Vision and Ophthalmology statement for the use of animals in ophthalmic and vision research and the protocols approved by the Institutional Animal Care and Use Committee.

Immunoblot analysis Protein samples were separated by SDS-PAGE and transferred to an Immobilon-P membrane. The membrane was incubated in blocking buffer, primary antibody, and horseradish peroxidase-conjugated anti-rabbit or mouse IgG secondary antibody. Antibodies against RPE65 (63), LRAT (64, 65), FATP4 (66), β-actin, rhodopsin, M-opsin (MilliporeSigma Co.), S-opsin (Santa Cruz Biotechnology) were used as the primary antibodies. Immunoblots were visualized with the ECL Prime Western blotting detection reagent and ImageQuant LAS 4000 (48). Signal intensity of each band was quantified using ImageQuant TL software.

Retinoid analysis All tissue manipulations and retinoid analysis were done under dim red light. Retinoids in mouse ocular tissues homogenized with 20 mM HEPES buffer containing 150 mM hydroxylamine were extracted with hexane and analyzed by normal phase high-performance liquid chromatography (HPLC), as described previously (67). In brief, retinoids in hexane extractions were evaporated, dissolved in 100 μl of hexane, and separated on a silica column by elution of mobile phase on an Agilent 1100 HPLC system. Spectral data were acquired for all eluted peaks. Quantitation was performed by comparison of peak areas to calibration curves established with authentic retinoid standards. For analysis of the visual cycle rates, dark-adapted mice were exposed to 800 lux light for 5 min, then transferred to darkness. At different times (30~120 min), eyeballs were enucleated and retinoids were extracted for HPLC analysis.

Immunohistochemistry Mouse retinal cryosections prepared from the dorsalventral midline of mouse eyes were immunostained as described previously (68). Briefly, mouse eyeballs were fixed with 4% paraformaldehyde in 0.1 M phosphate buffer (PB). After removing cornea and lens, eyecups were immersed in 15% sucrose in PB for 2 h and in 30% sucrose in PB overnight at 4° C., embedded in the OCT medium. Sections cut on a cryostat were immunostained with the primary antibodies and secondary antibodies. Nuclei were counterstained with DAPI. Images were captured with a Zeiss LSM710 Meta confocal microscope. Numbers of cone cells were counted using ImageJ software.

Quantification of S-opsin mislocalization Immunostaining of S-opsin was performed on retinal cryosections of 2-month-old mice, as described above. Fluorescence intensities in the outer segments (OS) and the retinal outer plexiform layer (OPL) were measured using an Olympus BX61VS microscope. We determined the fraction of mislocalized S-opsin according to the following formula. Mislocalization=[OPL fluorescence/(OS fluorescence+OPL fluorescence)]×100%.

Protease inhibitor assay Eyes were enucleated from euthanized 4-week-old mice, and the corneas and lenses were removed. The neural retinas dissected from the eyecups were maintained in the DMEM-F12 medium (Thermo Fisher Scientific Inc.) supplemented with 10% fetal bovine serum and antibiotics in a 5% CO2 incubator at 37° C. After incubating for 5 hours in the presence of a series of increasing concentrations of MG132 (0~25 μM) or pepstatin A (0~30 μM), the retinas were subjected to immunoblot analysis.

Quantification of soluble and insoluble opsins Retinas were homogenized in ice-cold PBS containing 0.4% Triton X-100 (Tx) and EDTA-free protease inhibitor cocktails. The homogenates containing 100 μg proteins were separated into supernatant and pellet by centrifugation at 100,000×g for 20 min at 4° C. The pellet was washed twice with ice-cold PBS and resuspended in 20 μl lysis buffer (PBS, 0.1% SDS and 0.4% Tx). Ten microliters of the resuspended pellet and the supernatant containing soluble proteins were subjected to immunoblot analysis. Percent of soluble and insoluble opsin was calculated using the following formula. Soluble or insoluble opsin %=[immunoblot intensity in soluble (or insoluble) fraction/sum of immunoblot intensities in soluble and insoluble fractions]×100%.

ERG Dark-adapted mice were anesthetized with an i.p. injection of Ketamine-Xylazine mixture and the pupils were dilated with 1% tropicamide. ERG was recorded from the corneal surface using a silver-silver chloride wire electrode referenced to a subcutaneous electrode in the mouth. A needle electrode in the tail served as the ground. A drop of 2.5% methylcellulose was placed on the cornea. ERG recordings were performed in a Ganzfeld dome (Espion e2, Diagnosys LLC) with various intensities of single flash stimuli (−4 log cd·s/$m^2$~2.4 log cd·s/$m^2$). For photopic ERGs, animals were light adapted for 10 min by exposing to 32 cd/$m^2$ light, and ERG responses were obtained with white flashes on the rod-saturating background (32 cd/$m^2$). For recording S- and M-cone ERG responses, animals were light adapted for 10 min by exposing to 40 cd/$m^2$ white light. S-cone ERGs were obtained with xenon flashes equipped with a Hoya U-360 filter on the 40 cd/$m^2$ background, and M-cone ERGs were elicited with stimuli of 530-nm light. Intensity-response amplitude data were displayed on log-linear coordinates using the SigmaPlot 11 software.

Statistical analysis All statistical analyses were performed using the SigmaPlot Version 11 (Systat Software, Inc.). Data were expressed as the mean±standard deviation (SD) of three or more independent experiments. Significant differences between distinct genotypes of mice were determined by single comparisons with an unpaired two-tailed Students t-test. The significance threshold was set at 0.05 for all statistical tests.

REFERENCES CITED IN THIS EXAMPLE

1. T. M. Redmond et al., Rpe65 is necessary for production of 11-cis-vitamin A in the retinal visual cycle. Nat. Genet. 20, 344-351 (1998).
2. M. Jin, S. Li, W. N. Moghrabi, H. Sun, G. H. Travis, Rpe65 is the retinoid isomerase in bovine retinal pigment epithelium. Cell 122, 449-459 (2005).
3. G. Moiseyev, Y. Chen, Y. Takahashi, B. X. Wu, J. X. Ma, RPE65 is the isomerohydrolase in the retinoid visual cycle. Proc. Natl. Acad. Sci. U.S.A. 102, 12413-12418 (2005).
4. T. M. Redmond et al., Mutation of key residues of RPE65 abolishes its enzymatic role as isomerohydrolase in the visual cycle. Proc. Natl. Acad. Sci. U.S.A. 102, 13658-13663 (2005).
5. B. Rohrer et al., Cone opsin mislocalization in Rpe65−/− mice: a defect that can be corrected by 11-cis retinal. Invest. Ophthalmol. Vis. Sci. 46, 3876-3882 (2005).
6. H. Zhang et al., Trafficking of membrane-associated proteins to cone photoreceptor outer segments requires the chromophore 11-cis-retinal. J. Neurosci. 28, 4008-4014 (2008).
7. R. Shyam, A. Gorusupudi, K. Nelson, M. P. Horvath, P. S. Bernstein, RPE65 has an additional function as the lutein to meso-zeaxanthin isomerase in the vertebrate eye. Proc. Natl. Acad. Sci. U.S.A. 114, 10882-10887 (2017).
8. P. S. Bernstein et al., Lutein, zeaxanthin, and meso-zeaxanthin: The basic and clinical science underlying carotenoid-based nutritional interventions against ocular disease. Prog. Retin. Eye Res. 50, 34-66 (2016).
9. A. Wenzel, C. E. Reme, T. P. Williams, F. Hafezi, C. Grimm, The Rpe65 Leu450Met variation increases retinal resistance against light-induced degeneration by slowingrhodopsin regeneration. J. Neurosci. 21, 53-58 (2001).
10. S. Li et al., Ciliary neurotrophic factor (CNTF) protects retinal cone and rod photoreceptors by suppressing excessive formation of the visual pigments. J. Biol. Chem. 293, 15256-15268 (2018).
11. S. R. Kim et al., Rpe65 Leu450Met variant is associated with reduced levels of the retinal pigment epithelium lipofuscin fluorophores A2E and iso-A2E. Proc. Natl. Acad. Sci. U.S.A. 101, 11668-11672 (2004).
12. J. Weng et al., Insights into the function of Rim protein in photoreceptors and etiology of Stargardt's disease from the phenotype in abcr knockout mice. Cell 98, 13-23 (1999).
13. S. Schmitz-Valckenberg et al., Correlation between the area of increased autofluorescence surrounding geographic atrophy and disease progression in patients with AMD. Invest. Ophthalmol. Vis. Sci. 47, 2648-2654 (2006).
14. S. G. Jacobson et al., Identifying photoreceptors in blind eyes caused by RPE65 mutations: Prerequisite for human gene therapy success. Proc. Natl. Acad. Sci. U.S.A. 102, 6177-6182 (2005).
15. S. G. Jacobson et al., Defining the residual vision in leber congenital amaurosis caused by RPE65 mutations. Invest. Ophthalmol. Vis. Sci. 50, 2368-2375 (2009).
16. S. G. Jacobson et al., Human cone photoreceptor dependence on RPE65 isomerase. Proc. Natl. Acad. Sci. U.S.A. 104, 15123-15128 (2007).
17. J. W. Bainbridge et al., Effect of gene therapy on visual function in Leber's congenital amaurosis. N. Engl. J. Med. 358, 2231-2239 (2008).
18. A. V. Cideciyan et al., Human gene therapy for RPE65 isomerase deficiency activates the retinoid cycle of vision but with slow rod kinetics. Proc. Natl. Acad. Sci. U.S.A 105, 15112-15117 (2008).
19. W. W. Hauswirth et al., Treatment of leber congenital amaurosis due to RPE65 mutations by ocular subretinal injection of adeno-associated virus gene vector: shortterm results of a phase I trial. Hum. Gene Ther. 19, 979-990 (2008).
20. A. M. Maguire et al., Safety and efficacy of gene transfer for Leber's congenital amaurosis. N. Engl. J. Med. 358, 2240-2248 (2008).
21. A. V. Cideciyan et al., Human retinal gene therapy for Leber congenital amaurosis shows advancing retinal degeneration despite enduring visual improvement. Proc. Natl. Acad. Sci. U.S.A. 110, E517-525 (2013).
22. S. G. Jacobson et al., Improvement and decline in vision with gene therapy in childhood blindness. N. Engl. J. Med. 372, 1920-1926 (2015).
23. J. W. Bainbridge et al., Long-term effect of gene therapy on Leber's congenital amaurosis. N. Engl. J. Med. 372, 1887-1897 (2015).
24. W. Xiong et al., AAV cis-regulatory sequences are correlated with ocular toxicity. Proc. Natl. Acad. Sci. U.S.A. 116, 5785-5794 (2019).
25. S. Li, M. Samardzija, Z. Yang, C. Grimm, M. Jin, Pharmacological Amelioration of Cone Survival and Vision in a Mouse Model for Leber Congenital Amaurosis. J. Neurosci. 36, 5808-5819 (2016).
26. S. Li et al., Rescue of Enzymatic Function for Disease-associated RPE65 Proteins Containing Various Missense Mutations in Non-active Sites. J. Biol. Chem. 289, 18943-18956 (2014).
27. S. Li et al., Temperature-sensitive retinoid isomerase activity of RPE65 mutants associated with Leber Congenital Amaurosis. J Biochem 158, 115-125 (2015).
28. S. Li et al., Fatty acid transport protein 4 (FATP4) prevents light-induced degeneration of cone and rod photoreceptors by inhibiting RPE65 isomerase. J. Neurosci. 33, 3178-3189 (2013).
29. K. Milger et al., Cellular uptake of fatty acids driven by the ER-localized acyl-CoA synthetase FATP4. J. Cell Sci. 119, 4678-4688 (2006).
30. A. M. Hall, B. M. Wiczer, T. Herrmann, W. Stremmel, D. A. Bernlohr, Enzymatic properties of purified murine fatty acid transport protein 4 and analysis of acyl-CoA synthetase activities in tissues from FATP4 null mice. J. Biol. Chem. 280, 11948-11954 (2005).
31. Z. Jia, C. L. Moulson, Z. Pei, J. H. Miner, P. A. Watkins, Fatty acid transport protein 4 is the principal very long chain fatty acyl-CoA synthetase in skin fibroblasts. J. Biol. Chem. 282, 20573-20583 (2007).
32. S. Li, J. F. Green, M. Jin, Impacts of deletion and ichthyosis prematurity syndrome associated mutations in fatty acid transport protein 4 on the function of RPE65. FEBS Lett. 594, 540-552 (2020).
33. S. G. Jacobson et al., Photoreceptor layer topography in children with leber congenital amaurosis caused by RPE65 mutations. Invest. Ophthalmol. Vis. Sci. 49, 4573-4577 (2008).
34. M. Samardzija et al., In conditions of limited chromophore supply rods entrap 11-cisretinal leading to loss of cone function and cell death. Hum. Mol. Genet. 18, 1266-1275 (2009).

35. M. Lee, S. Li, K. Sato, M. Jin, Interphotoreceptor Retinoid-Binding Protein Mitigates Cellular Oxidative Stress and Mitochondrial Dysfunction Induced by All-trans-Retinal. Invest. Ophthalmol. Vis. Sci. 57, 1553-1562 (2016).
36. J. Fan, B. Rohrer, G. Moiseyev, J. X. Ma, R. K. Crouch, Isorhodopsin rather than rhodopsin mediates rod function in RPE65 knock-out mice. Proc. Natl. Acad. Sci. U.S.A. 100, 13662-13667 (2003).
37. M. Samardzija et al., R91W mutation in Rpe65 leads to milder early-onset retinal dystrophy due to the generation of low levels of 11-cis-retinal. Hum. Mol. Genet. 17, 281-292 (2008).
38. A. Szel et al., Unique topographic separation of two spectral classes of cones in the mouse retina. J. Comp. Neurol. 325, 327-342 (1992).
39. P. D. Kiser, M. Golczak, D. T. Lodowski, M. R. Chance, K. Palczewski, Crystal structure of native RPE65, the retinoid isomerase of the visual cycle. Proc. Natl. Acad. Sci. U.S.A. 106, 17325-17330 (2009).
40. P. Chen et al., A photic visual cycle of rhodopsin regeneration is dependent on Rgr. Nat. Genet. 28, 256-260 (2001).
41. A. Morshedian et al., Light-Driven Regeneration of Cone Visual Pigments through a Mechanism Involving RGR Opsin in Muller Glial Cells. Neuron 102, 1172-1183 e1175 (2019).
42. J. Zhang et al., Photic generation of 11-cis-retinal in bovine retinal pigment epithelium. J. Biol. Chem. 294, 19137-19154 (2019).
43. G. M. Acland et al., Long-term restoration of rod and cone vision by single dose rAAVmediated gene transfer to the retina in a canine model of childhood blindness. Mol Ther 12, 1072-1082 (2005).
44. S. L. Znoiko et al., Downregulation of cone-specific gene expression and degeneration of cone photoreceptors in the Rpe65−/− mouse at early ages. Invest. Ophthalmol. Vis. Sci. 46, 1473-1479 (2005).
45. C. Jakobsson, I. S. Othman, F. L. Munier, D. F. Schorderet, H. Abouzeid, Cone-rod dystrophy caused by a novel homozygous RPE65 mutation in Leber congenitalamaurosis. Klin Monbl Augenheilkd 231, 405-410 (2014).
46. R. S. Saliba, P. M. Munro, P. J. Luthert, M. E. Cheetham, The cellular fate of mutant rhodopsin: quality control, degradation and aggresome formation. J. Cell Sci. 115, 2907-2918 (2002).
47. Z. Zhou, D. Vollrath, A cellular assay distinguishes normal and mutant TIGR/myocilin protein. Hum. Mol. Genet. 8, 2221-2228 (1999).
48. S. Li et al., Secretory defect and cytotoxicity: the potential disease mechanisms for the retinitis pigmentosa (RP)-associated interphotoreceptor retinoid-binding protein (IRBP). J. Biol. Chem. 288, 11395-11406 (2013).
49. J. H. Lin et al., IRE1 signaling affects cell fate during the unfolded protein response. Science 318, 944-949 (2007).
50. K. Sato, T. Ozaki, S. Ishiguro, M. Nakazawa, M-opsin protein degradation is inhibited by MG-132 in Rpe65(−)/(−) retinal explant culture. Mol. Vis. 18, 1516-1525 (2012).
51. T. Zhang, N. Zhang, W. Baehr, Y. Fu, Cone opsin determines the time course of cone photoreceptor degeneration in Leber congenital amaurosis. Proc. Natl. Acad. Sci. U.S.A. 108, 8879-8884 (2011).
52. C. Punzo, K. Kornacker, C. L. Cepko, Stimulation of the insulin/mTOR pathway delays cone death in a mouse model of retinitis pigmentosa. Nat. Neurosci. 12, 44-52 (2009).
53. J. Won et al., Mouse model resources for vision research. J Ophthalmol 2011, 391384 (2011).
54. C. B. Wright et al., Complementation test of Rpe65 knockout and tvrm148. Invest. Ophthalmol. Vis. Sci. 54, 5111-5122 (2013).
55. Y. Li et al., Mouse model of human RPE65 P25L hypomorph resembles wildtype under normal light rearing but is fully resistant to acute light damage. Hum. Mol. Genet. 10.1093/hmg/ddv178 (2015).
56. B. Lorenz et al., A comprehensive clinical and biochemical functional study of a novel RPE65 hypomorphic mutation. Invest. Ophthalmol. Vis. Sci. 49, 5235-5242 (2008).
57. A. R. Philp et al., Predicting the pathogenicity of RPE65 mutations. Hum. Mutat. 30, 1183-1188 (2009).
58. B. Li et al., Inactivity of human beta,beta-carotene-9',10'-dioxygenase (BCO2) underlies retinal accumulation of the human macular carotenoid pigment. Proc. Natl. Acad. Sci. U.S. A. 111, 10173-10178 (2014).
59. B. Li et al., Retinal accumulation of zeaxanthin, lutein, and beta-carotene in mice deficient in carotenoid cleavage enzymes. Exp. Eye Res. 159, 123-131 (2017).
60. E. D. Labonte et al., Reduced absorption of saturated fatty acids and resistance to dietinduced obesity and diabetes by ezetimibe-treated and Npc1l1−/− mice. Am J Physiol Gastrointest Liver Physiol 295, G776-783 (2008).
61. M. Naples et al., Ezetimibe ameliorates intestinal chylomicron overproduction and improves glucose tolerance in a diet-induced hamster model of insulin resistance. Am J Physiol Gastrointest Liver Physiol 302, G1043-1052 (2012).
62. C. L. Moulson et al., Keratinocyte-specific expression of fatty acid transport protein 4 rescues the wrinkle-free phenotype in Slc27a4/Fatp4 mutant mice. J. Biol. Chem. 282, 15912-15920 (2007).
63. M. Jin, Q. Yuan, S. Li, G. H. Travis, Role of LRAT on the retinoid isomerase activity and membrane association of Rpe65. J. Biol. Chem. 282, 20915-20924 (2007).
64. M. L. Batten et al., Lecithin-retinol acyltransferase is essential for accumulation of alltrans-retinyl esters in the eye and in the liver. J. Biol. Chem. 279, 10422-10432 (2004).
65. M. Golczak, V. Kuksa, T. Maeda, A. R. Moise, K. Palczewski, Positively charged retinoids are potent and selective inhibitors of the trans-cis isomerization in the retinoid (visual) cycle. Proc. Natl. Acad. Sci. U.S.A. 102, 8162-8167 (2005).
66. E. P. Newberry et al., Decreased hepatic triglyceride accumulation and altered fatty acid uptake in mice with deletion of the liver fatty acid-binding protein gene. J. Biol. Chem. 278, 51664-51672 (2003).
67. M. Jin et al., The role of interphotoreceptor retinoid-binding protein on the translocation of visual retinoids and function of cone photoreceptors. J. Neurosci. 29, 1486-1495 (2009).
68. K. Sato et al., Receptor interacting protein kinase-mediated necrosis contributes to cone and rod photoreceptor degeneration in the retina lacking interphotoreceptor retinoid binding protein. J. Neurosci. 33, 17458-17468 (2013).

Example 3

Example 3—Ezetimibe for Retinal Degenerations

Ezetimibe is an FDA-approved lipid-lowering agent that blocks NPC1L1 (NPC1 like intracellular cholesterol transporter 1)-dependent cholesterol transport at the border of the intestine and inhibits absorption of dietary and biliary cholesterols. Described herein are studies utilizing Ezetimibe and the statin Simvastatin, an HMG-CoA reductase inhibitor.

Figure 9:
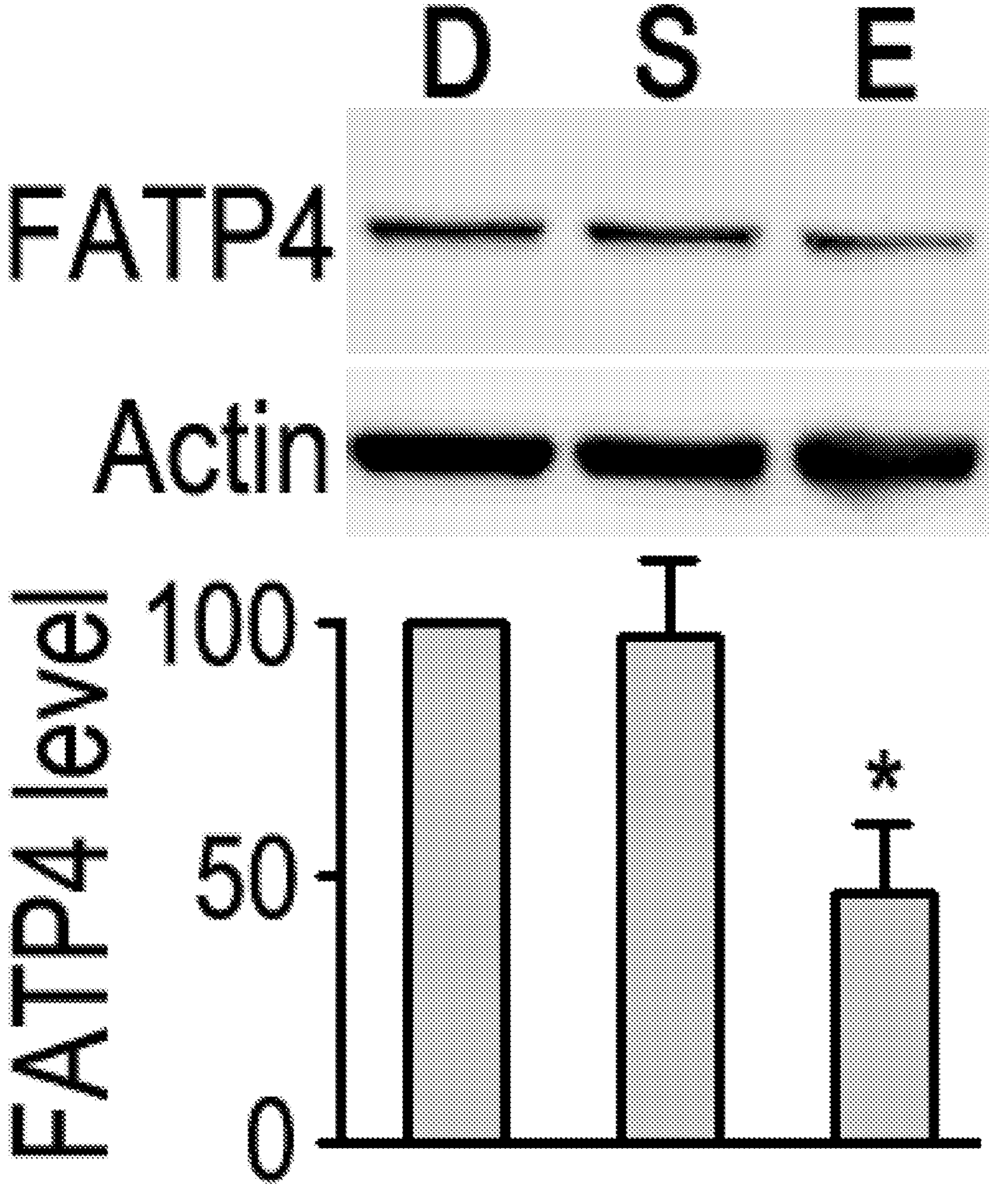
FIG. 9 shows immunoblot analysis of FATP4 and actin proteins in the retinal pigment epithelium (RPE) of one-month-old mice treated daily as follows: Lane D: DMSO (1 ml/kg), lane S: Simvastatin (30 mg/kg), lane E: Ezetimibe (10 mg/kg). Error bars denote standard deviation, * $p<0.05$. Actin was detected as the loading control.
Figure 10:
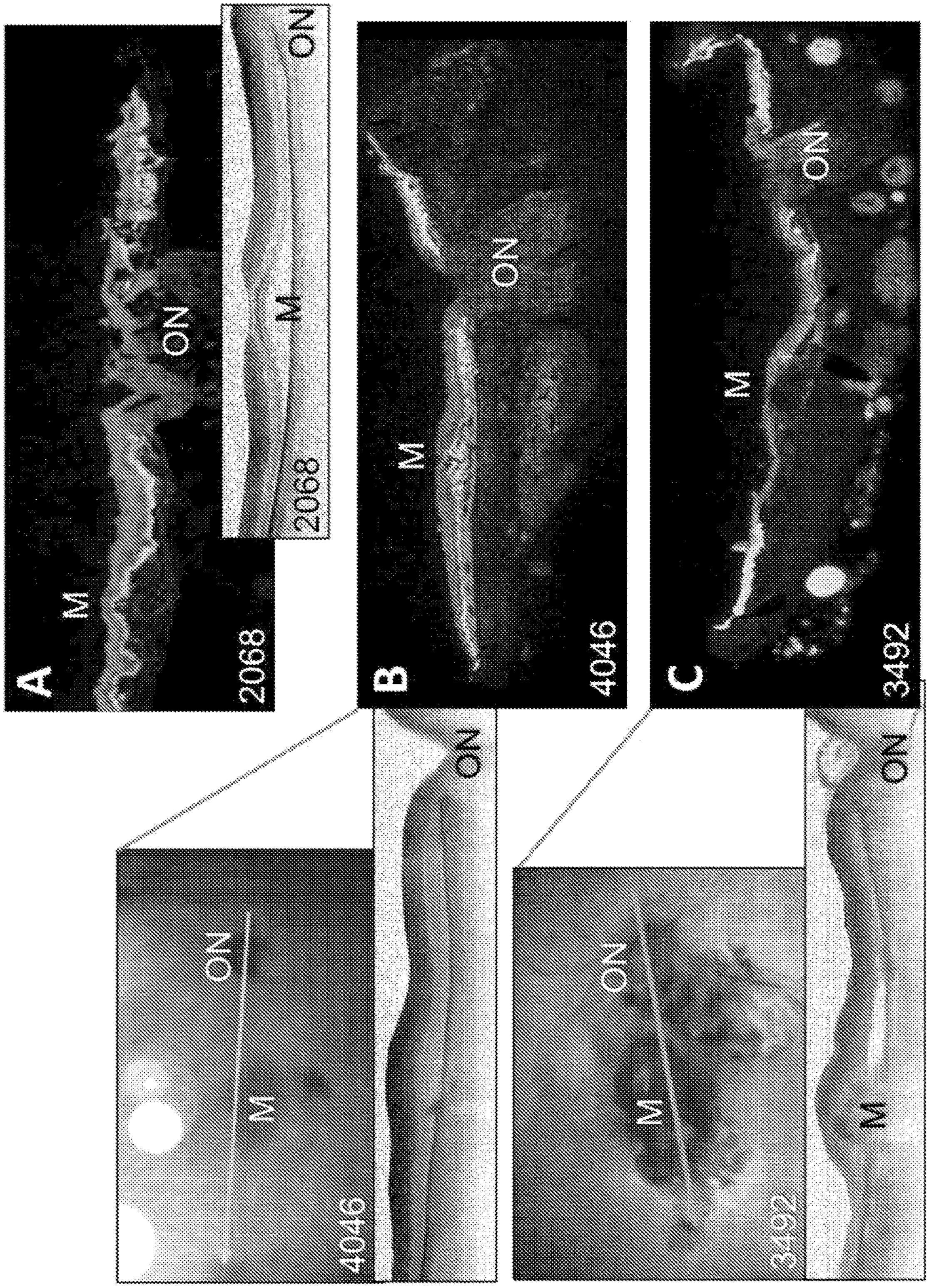
FIG. 10 shows fundus, OCT, and MALDI images taken from a patient that has not been diagnosed with a retinal degenerative disease (A), a patient with an early form of retinal degenerative disease (B), and a patient with advanced retinal degenerative disease (C). Panel A shows images from a normal 84-year-old human retina showing a color MALDI image, and an OCT image. MALDI imaging reveals distinct layering within the retina; m/z 810 (red) occurs within the optic nerve and the inner retina, m/z 818 (blue) is localized to the macular region (and can indicate cone photoreceptor bipolar cells), and m/z 856 (green) is found in the photoreceptor layer, but is displaced distally into the region of inner/outer segments. In Panel A, the OCT image of the retina shows the macula region near the center. Panel B shows images from an 83-year-old human retina with early Macular Degeneration showing a MALDI, an OCT, and a fundus image, respectively, at right. In Panel B, the color MALDI image reveals the m/z 810 (red), the m/z 818 (blue) most concentrated in the macula, and the m/z 856 (green) photoreceptor layer, showing some disruption along the retina. This affected region in Panel B is also apparent in the fundus and OCT images. Panel C shows images from a 101-year-old human retina with advanced Macular Degeneration. The data from Panel C show a severely distressed retina. In Panel C, the color MALDI image reveals extensive loss of photoreceptors (green layer). Both the OCT and fundus images of Panel C depict widespread retinal damage. The green arrow in the fundus images of B and C represent the path of the scan through the retina for their respective OCT images. ON, optic nerve; CF, Caucasian female; CM, Caucasian male; M, macula.
Figure 11:
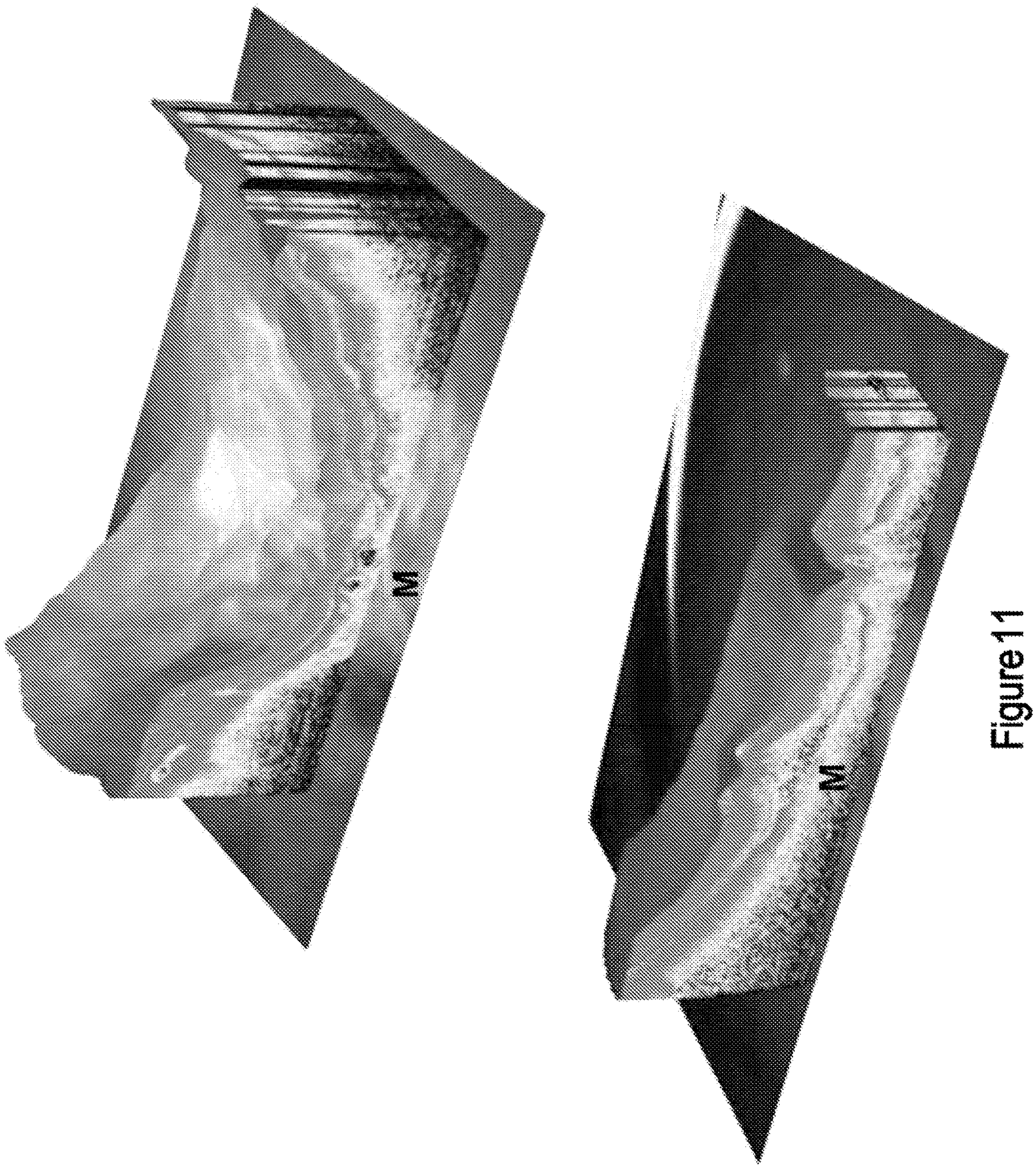
FIG. 11 provides OCT imaging showing a normal human retina (top) with the Macula (M), and a human retina with Geographic atrophy (bottom). The shiny white area is a reflection.
Figure 12:
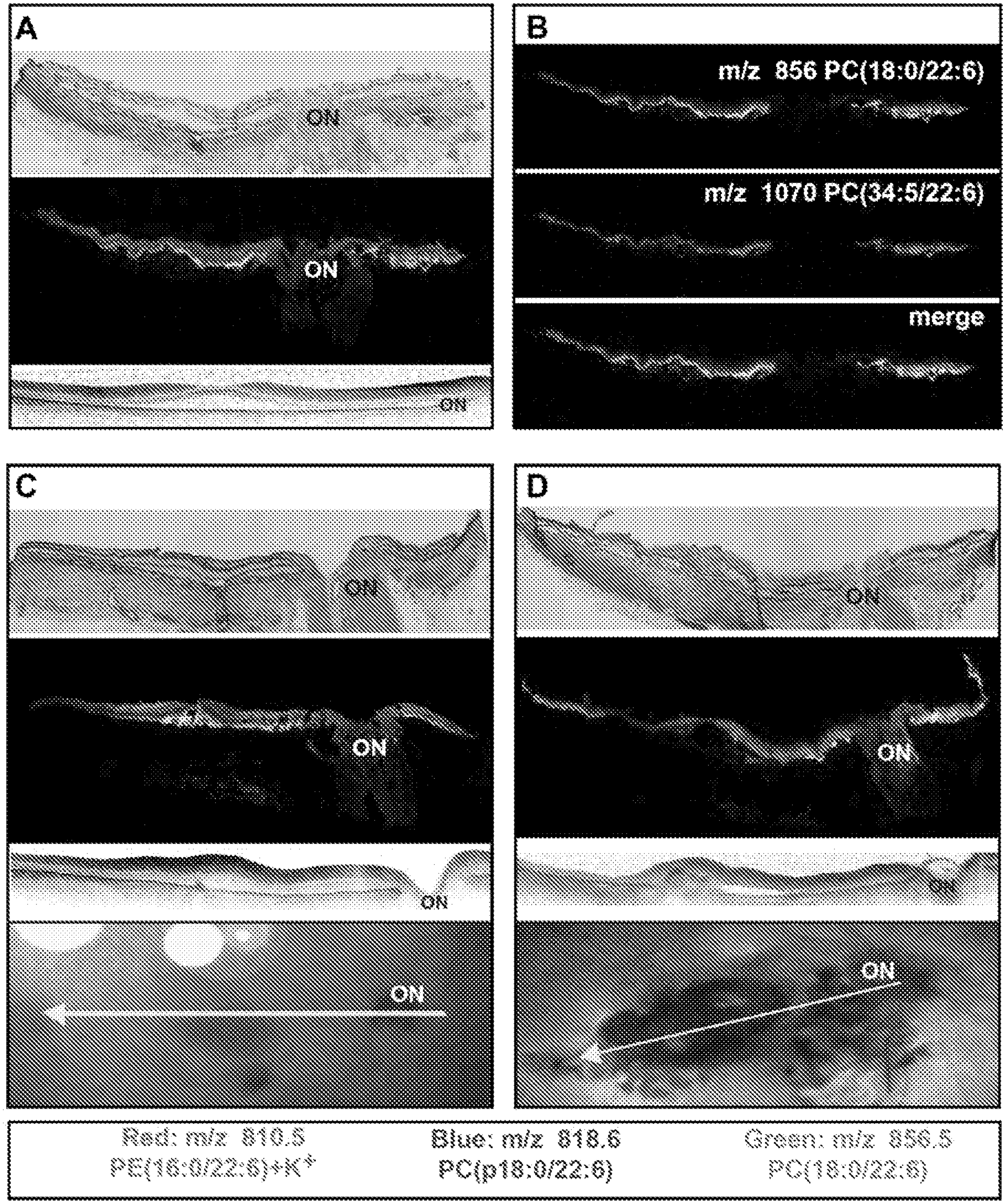
FIG. 12 shows histological (top), MALDI (second image), OCT (third image) images taken from a patient that has not been diagnosed with a retinal degenerative disease (A), a patient with an early form of retinal degenerative disease (C), and a patient with advanced retinal degenerative disease (D). Panels C and D further include an image of the fundus (bottom image), and the green arrow in the fundus images of C and D represent the path of the scan through the retina for their respective OCT images. ON, optic nerve. MALDI imaging reveals distinct layering within the retina; m/z 810 (red) occurs within the optic nerve and the inner retina, m/z 818 (blue) is localized to the macular region (and can indicate cone photoreceptor bipolar cells), and m/z 856 (green) is found in the photoreceptor layer. Panel B shows additional MALDI imaging from the patent in panel A with m/z shown in green at the top, m/z 1070 shown in red in the middle, and the bottom shows a merged image of the top and bottom panels.

As shown in FIG. 9, we found that oral administration of Ezetimibe reduced expression levels of fatty acid transport protein 4 (FATP4), an inhibitor of RPE65 isomerase, in the retinal pigment epithelium (RPE). Simvastatin was devoid of an effect demonstrating specificity. This is in agreement with the data in our studies that showed that FATP4 reduction could alleviate photoreceptor degeneration and vision loss in an animal model of retinal degenerative diseases caused by a mutation in the Rpe65 gene. Without wishing to be bound by theory, Ezetimibe treatment can improve vision and photoreceptor survival in patients with RPE65 mutations that engages several groups of retinal degenerative diseases as listed below.

Due to advances in viral vector technology, gene therapy has led the FDA to approve the first gene therapy targeting a disease caused by mutations of RPE65: LUXTURNA™ (voretigene neparvovec-rzyl; Spark Therapeutics, Inc., Philadelphia, PA). This gene therapy delivers a copy of the RPE65 gene to the retina for the treatment of RPE65 mutation-associated retinal dystrophy.

Without wishing to be bound by theory, Ezetimibe alone or in combination with gene therapy can be of use at least in the following diseases:

Leber congenital amaurosis (LCA)
Autosomal recessive retinitis pigmentosa (ARRP)
Early-onset severe rod-cone dystrophy
Autosomal dominant retinitis pigmentosa

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of treating or preventing a retinal degenerative disease in a subject with an RPE65 mutation, the method comprising administering to the subject an effective amount of a composition comprising ezetimibe.

2. A method of treating a missense mutation disease in a subject with an RPE65 mutation, the method comprising administering to the subject an effective amount of a composition comprising ezetimibe.

3. A method of treating a mutation-associated retinal dystrophy in a subject with an RPE65 mutation, the method comprising administering to the subject an effective amount of a composition comprising ezetimibe.

4. The method of any one of claims 1-3, wherein the disease or dystrophy comprises an RPE65 mutation-associated retinal dystrophy, Leber congenital amaurosis (LCA), autosomal recessive retinitis pigmentosa (ARRP), early-onset severe rod-cone dystrophy, or autosomal dominant retinitis pigmentosa.

5. A method of decreasing fatty acid transport protein 4 (FATP4) expression in a subject with an RPE65 mutation, the method comprising administering to the subject an effective amount of a composition comprising ezetimibe.

6. A method of preventing loss of phototransduction in a subject with an RPE65 mutation, the method comprising administering to the subject an effective amount of a composition comprising ezetimibe.

7. A method of increasing the synthesis of cis-retinals in a subject with an RPE65 mutation, the method comprising administering to the subject an effective amount of a composition comprising ezetimibe.

8. The method of claim 7, wherein the cis-retinals comprise 11-cis-retinal or 9-cis-retinal.

9. A method of alleviating cone degeneration or color vision loss in patients with RPE65 mutations, the method comprising administering to the subject an effective amount of a composition comprising ezetimibe.

10. A method of decreasing the photoreceptor degeneration or death in a subject with an RPE65 mutation, the method comprising administering to the subject an effective amount of a composition comprising ezetimibe.

11. A method of preserving visual cycle rate in a subject with an RPE65 mutation, the method comprising administering to the subject an effective amount of a composition comprising ezetimibe.

12. The method of any one of claim 1-3, 5-7, or 9-11, wherein the composition further comprises at least one of 4-phenylbutyrate or a gene therapy agent.

13. The method of claim 12, wherein the gene therapy agent comprises AAV-RPE65 or voretigene naparvovec-rzyl.

14. A pharmaceutical composition comprising an effective amount of a combination of ezetimibe, a therapeutically acceptable carrier, and at least one of 4-phenylbutyrate or a gene therapy agent.

15. The composition of claim 14, wherein the gene therapy agent comprises AAV-RPE65 or voretigene naparvovec-rzyl.

* * * * *